US012591840B2

(12) United States Patent
O'Toole et al.

(10) Patent No.:  US 12,591,840 B2
(45) Date of Patent:       Mar. 31, 2026

(54) DEVICE AND SYSTEM FOR AN AUTONOMOUS MOBILE ROBOT, DRONE, AND/OR COURIER TO DELIVER, HOLD, PROTECT, AND RETURN PARCELS FOR MULTI-USERS IN BOTH RESIDENTIAL AND COMMERCIAL APPLICATIONS

(71) Applicants: Daniel S O'Toole, Carmel, IN (US);
Torrey M. Bievenour, Indianapolis, IN
(US); Neerav Shah, Indianapolis, IN
(US); Mark Hamm, Germantown, TN
(US); John D Ritchison, Anderson, IN
(US)

(72) Inventors: Daniel S O'Toole, Carmel, IN (US);
Torrey M. Bievenour, Indianapolis, IN
(US); Neerav Shah, Indianapolis, IN
(US); Mark Hamm, Germantown, TN
(US); John D Ritchison, Anderson, IN
(US)

( * ) Notice: Subject to any disclaimer, the term of this patent is extended or adjusted under 35 U.S.C. 154(b) by 527 days.

(21) Appl. No.: 18/208,803

(22) Filed: Jun. 12, 2023

(65) Prior Publication Data

US 2023/0410028 A1     Dec. 21, 2023

Related U.S. Application Data

(60) Provisional application No. 63/352,574, filed on Jun. 15, 2022.

(51) Int. Cl.
*G06F 7/00*        (2006.01)
*A61L 2/24*        (2006.01)
(Continued)

(52) U.S. Cl.
CPC ............ *G06Q 10/0833* (2013.01); *A61L 2/24* (2013.01); *B60Q 5/005* (2013.01); *B64D 47/02* (2013.01);
(Continued)

(58) Field of Classification Search
CPC ............ G06Q 10/0833; G06Q 10/083; G06Q 10/0832; G06Q 10/08365; G06Q 10/0836;
(Continued)

(56) References Cited

U.S. PATENT DOCUMENTS 12,205,072 B1 *    1/2025   Mohammed ......... G06Q 10/083

\* cited by examiner

*Primary Examiner* — Yolanda R Cumbess
(74) *Attorney, Agent, or Firm* — Ritchison Law Offices PC; John D Ritchison

(57)                    ABSTRACT
A device and system for an automatic robot, drone, and/or courier to deliver, hold, protect, and return parcels. The multi-user system has DRONEDEK docking features and include a small footprint combination; nine to 400 parcel capacity; has a multi-belt conveyor and turntables for parcels; uses omni-directional and cross roller turns; is compatible with re-usable packaging; has a parcel tilt and reload for return packages; utilizes a lightweight frame; has secure outer skin and access panels for maintenance; communicates and is controlled by DRONEDEK docking station; can use robotic unload/pick and place, multiple delivery/receiving, and can attach to other third-party parcel systems. A multi-user box is quite simply a unit with the functionality of one or more DRONEDEK docking stations and features numerous/multiple pigeonholes and container spaces for safe, secure storage of items to separate and distinct users in a bulk location.

19 Claims, 25 Drawing Sheets

(51) Int. Cl.

| | |
|---|---|
| *B60Q 5/00* | (2006.01) |
| *B64D 47/02* | (2006.01) |
| *B64F 1/36* | (2017.01) |
| *B65G 1/137* | (2006.01) |
| *G06Q 10/0833* | (2023.01) |
| *B64U 101/66* | (2023.01) |

(52) U.S. Cl.
CPC .............. *B64F 1/368* (2013.01); *B65G 1/137*
(2013.01); *A61L 2202/11* (2013.01); *A61L*
*2202/14* (2013.01); *A61L 2202/16* (2013.01);
*A61L 2202/23* (2013.01); *B64U 2101/66*
(2023.01)

(58) Field of Classification Search
CPC ......... G06Q 10/0837; A61L 2/10; A61L 2/24;
A61L 2202/11; A61L 2202/14; A61L
2202/16; A61L 2202/23; A61L 2/202;
B60Q 5/005; B64D 47/02; B64F 1/368;
B65G 1/137; B65G 61/00; B65G 1/04;
B65G 1/0464; B65G 1/0485; B65G 1/06;
B65G 15/00; B65G 17/30; B65G 17/32;
B65G 43/00; B65G 47/00; B65G 47/52;
B65G 47/90; B65G 69/00; B65G 1/00;
B65G 1/02; B65G 1/026; B65G 47/53;
B65G 47/57; B65G 47/71; B65G 1/023;
B64U 2101/66; B64U 50/39; B64U
70/95; B64U 2101/64; B64U 10/14;
B64U 50/37; B64U 70/90; B64U
2101/31; B64U 2201/104; G07F 11/58;
G07F 17/13; G07F 17/10; G06K 7/10237;
G06K 19/06009; G06K 2017/0051; G08B
5/36; H04W 4/80; H04W 12/03
USPC .................................................. 700/213–215
See application file for complete search history.

Figures 1A, 1B, 1C:
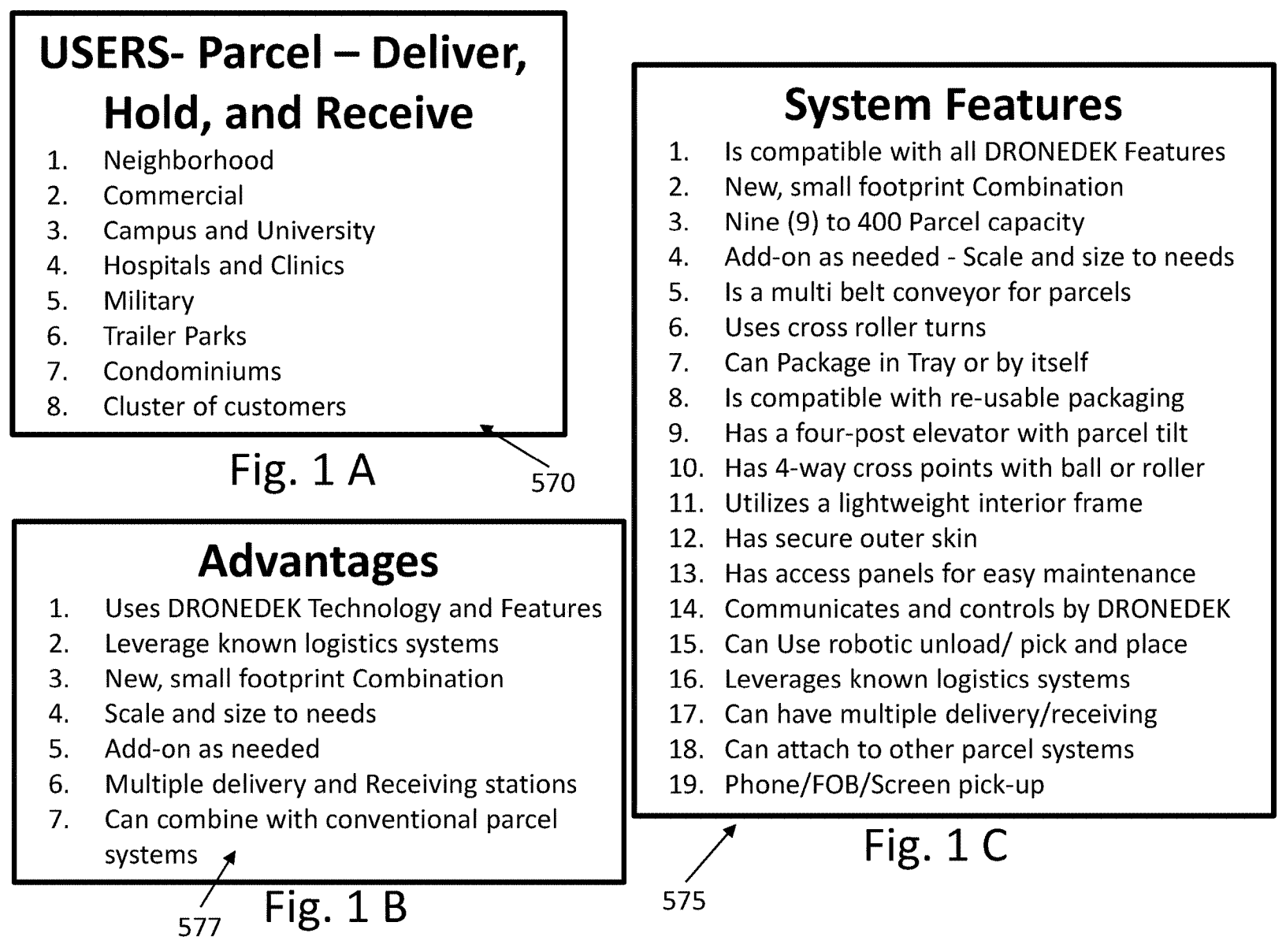

USERS- Parcel – Deliver, Hold, and Receive

1. Neighborhood
2. Commercial
3. Campus and University
4. Hospitals and Clinics
5. Military
6. Trailer Parks
7. Condominiums
8. Cluster of customers

System Features

1. Is compatible with all DRONEDEK Features
2. New, small footprint Combination
3. Nine (9) to 400 Parcel capacity
4. Add-on as needed - Scale and size to needs
5. Is a multi belt conveyor for parcels
6. Uses cross roller turns
7. Can Package in Tray or by itself
8. Is compatible with re-usable packaging
9. Has a four-post elevator with parcel tilt
10. Has 4-way cross points with ball or roller
11. Utilizes a lightweight interior frame
12. Has secure outer skin
13. Has access panels for easy maintenance
14. Communicates and controls by DRONEDEK
15. Can Use robotic unload/ pick and place
16. Leverages known logistics systems
17. Can have multiple delivery/receiving
18. Can attach to other parcel systems
19. Phone/FOB/Screen pick-up

Advantages

1. Uses DRONEDEK Technology and Features
2. Leverage known logistics systems
3. New, small footprint Combination
4. Scale and size to needs
5. Add-on as needed
6. Multiple delivery and Receiving stations
7. Can combine with conventional parcel systems

Isometric of Chambers with Belt transfers

Note: Controls, chains, structure,
Connections are similar to Figures 11-19

Optional Robotic
Pick & Place 180
not shown

Front access panel removed

Side View
of Chambers
with Belt transfers
Optional Robotic Pick &
Place not shown Note: Controls, chains, structure,
Connections are similar to Figures 11-19

NOTE: Can make more
Chambers High and deep

Table Sorter

Optional Robotic Pick & Place not shown. Note: Controls, chains, structure, Connections are similar to Figures 11-19

DRONEDEK Connect with
Third party system
Optional Robotic Pick
& Place 180  not shown

569

180

40

565

567

Note: Controls, chains, structure,
Connections are similar to Figures 11-19

50

40

34

535

552

530

35

530

Front access
panel removed

Table Sorter with Chamber Sketches

Fig. 7 A — Sketches of Belt Transfer with Chamber Sketches

Belt Chamber Cross-sections
Early Sketches

Chamber Cross-sections
Early Sketches

Entry Control PANEL

Multi Lockbox Prior Art

CNTL

Multi Lockbox Prior Art

131,30

131

131P

131DS

180

This Page All
Prior Art

End for Roll-out
132E Not Shown

This Page
All Prior Art

Repeated

This Page
All Prior Art

This Page
All Prior Art

DRONEDEK

Curb

6309

131P

131DS

131DS

131DS

This Page
All Prior Art

Barcode reader

73

1　2　3

This Page
All Prior Art

50

83
84
85
82
81 76
131

Ultra Violet detox

125

1　2　3

1. Enter

2. Start Cloud

3. Full Encircle

4. Clean

130 Ozone/
Disinfectant blast

656

Automated Door

Mailbox

User Door

Curb Side

Back Side

Gen 2

Open Drone Door/Funnel 652
for "Precision
Delivery/Pickup"

653

Opening for
Through bot 657

652

654

653

651

650

2 floors w/
Mecanum
wheel
or equal
moving floor
all directions
And elevate

Drop-through
Position 653

652

170
172
175
180
177
332FM
159
PS
C
M
66
131

132E
132B

This Page
All Prior Art

This Page
All Prior Art

DEVICE AND SYSTEM FOR AN AUTONOMOUS MOBILE ROBOT, DRONE, AND/OR COURIER TO DELIVER, HOLD, PROTECT, AND RETURN PARCELS FOR MULTI-USERS IN BOTH RESIDENTIAL AND COMMERCIAL APPLICATIONS

CROSS-REFERENCE TO RELATED APPLICATIONS

This application claims the benefit of U.S. Provisional Patent Application with Ser. No. 63/352,574 filed Jun. 15, 2022, by Daniel S. O'Toole. The provisional application is entitled "A device and system to Deliver, Hold, Protect, and Receive Parcels for multiusers residential and commercial application aka Cluster Box".

FIELD OF INVENTION

This invention relates to a device and system for an autonomous mobile robot (quadra-pods, automated guided vehicles, ground based pods, articulated robots, bipods, humanoids, etc.), drones, and/or courier to deliver, hold, protect, and return parcels for multi-users in both residential and commercial applications—a docking station called a DRONEDEK Multi-User Box. The invention relates to drones, couriers, and/or autonomous mobile robots (AMR) for the delivery of parcels or goods. The present application relates to a delivery location for receiving a package from a vehicle—drone or unmanned aerial vehicle (UAV), robotic carriers/couriers, or automated unmanned vehicle systems (AUVS) and AMRs. The present disclosure relates to a docking station for unmanned and drone aircraft, more specifically to landing and docking systems for unmanned aircraft to deliver and to receive goods to a multi-user parcel system. The embodiments of the disclosure relate to the field of aircraft and unmanned vehicular delivery, to a device for receiving and sending an article. A device for a drone docking station for deposit of items delivered by drone, robot or AUVs/AMRs. Items may include but not be limited to food items, groceries, and multi-use parcels. A secure porch, roof, window or otherwise building mounted box may be secured through to an existing edifice or may be configured to mount to an existing mailbox post and/or take the place of the mailbox. The invention relates to drones, couriers, and AMRs for delivery and return of parcels or goods.

FEDERALLY SPONSORED RESEARCH

None.

SEQUENCE LISTING OR PROGRAM

None.

BACKGROUND

Field of Invention and Prior Art

As far as known, there are no devices and systems to Deliver, Hold, Protect, and Return Parcels for multi-users residential and Commercial applications or the like. It is believed that this product is unique in its design and technologies. A background as to deliveries and the current industry and market should be useful. Unmanned aerial vehicles (UAVs) comprise a variety of vehicles, from conventional fixed wing airplanes, to helicopters, to ornithopters (i.e., machines that fly like birds), and are used in a variety of roles. They (delivery or return/pick-up devices and can be remotely piloted by a pilot on the ground or can be autonomous or semi-autonomous vehicles that make unmanned ground deliveries or fly missions using preprogrammed coordinates, GPS navigation, etc. UAVs/AMRs can include remote control helicopters and airplanes for the hobbyist, for example. UAVs/AMRs may be equipped with cameras to provide imagery during flight or traversing sidewalk, roads, or grounds, which may be used for navigational or other purposes, e.g., identify a house address, etc. Unmanned Aerial Vehicles (UAVs) and Autonomous Mobile Robots (AMRs) can also be equipped with sensors to provide local weather and atmospheric conditions, radiation levels, and other conditions. UAVs/AMRs may also include cargo bays, hooks, or other means for carrying payloads. Newer generation UAVs/AMRs may also provide significant payload capabilities. As a result, UAVs/AMRs can also be used for delivering packages, groceries, mail, and other items. The use of UAVs/AMRs for deliveries can reduce costs and increase speed and accuracy. The range provided by current UAVs/AMRs technology, however, makes deliveries over a wide area—e.g., throughout a city, or even a portion of a city-difficult.

Parcel transportation between an origin and a destination is traditionally a labor-intensive process. For short distance, "local" deliveries, an item (e.g., parcel) may be transported by a delivery person between the origin and the destination. For example, the delivery person/courier may drive a vehicle to transport the item between the origin and the destination and may ensure that the item is properly picked up and/or delivered according to specific delivery instructions required. For longer-distance deliveries, transportation of an item may involve several delivery methods and personnel, who may individually perform one or more steps for picking up an item, sorting the item one or more times, transporting the item from a final sort of location to a final delivery destination, and/or delivering the item from the delivery vehicle to the destination address (e.g., serviceable point). Because of the labor-intensive nature of this process, various attempts have been made to assist carrier personnel by reducing the physical demands required in the transportation and delivery process. However, prior attempts have faced substantial difficulties in ensuring that various aspects of the transportation and delivery process are properly performed. For example, attempts have been made to utilize unmanned vehicles, such as Unmanned Aerial Vehicles (UAVs) and AMRs to transport items from a final sort location to an intended final delivery destination. However, such concepts are generally limited by the effective range of the UAVs/AMRs, as well as the number of available UAVs/AMRs that may be utilized to deliver items to locations a substantial distance away from the final sort of location. Accordingly, a need exists for additional systems and methods to assist carrier/courier personnel and thereby reduce the physical demands of the transportation and delivery process.

Typically ordered items are packed in shipping packages (e.g., corrugated cardboard boxes or plastic bags and sacks) and shipped to the user's residence or place of business. Physical delivery of items to user specified locations has improved dramatically over the years, with some aggressive retailers offering next day delivery of ordered items. The final or last mile delivery of physical items to a user specified location is traditionally accomplished using a human controlled truck, bicycle, cart, etc. For example, a user may order an item for delivery to their home. The item may be picked from a ground-based material handling facility, packed, and shipped to the user for final delivery by a shipping carrier. The shipping carrier will load the item onto a truck that is driven by a human to the final delivery location and the human driver, or another human companion with the driver, will retrieve the item from the truck and complete the delivery to the destination. For example, the human may hand the item to a recipient, place the item on the user's porch, store the item in a post office box, etc. In these new times where the world is changing before one's very eyes, technology must keep up with consumer habits. Efficiency, cost savings, technology, convenience, ease, safety, and more combine to dictate where the US and world market economy is going.

One emerging sector of the economy is last mile logistics. Within this segment of the shipping economy is a rapidly developing facet known as drone delivery. Shifting metrics in the world's ecosystem dictate now, more than ever, the need for autonomous delivery. Enter DRONEDEK for drones, AMRs and AUVs delivering to multi-user locations. DRONEDEK currently holds several U.S. Utility Patents, and it continues to constantly build on its offerings. Every day in the US more than 1.7 million packages are stolen. The loss created is in the billions. DRONEDEK docking units at multi users helps solve this problem through encrypted, authenticated delivery. Every day in the US, thousands of packages are mis-shipped. DRONEDEK solves this problem through encrypted, authenticated delivery. In this new world, social distancing will be the "new normal". DRONEDEK docks allow shippers, deliverers, and recipients to practice social distancing all while increasing the user experience.

Millennials are a growing force in the US and world economy, and they have their own way of doing things. More and more people are working from home, venturing out less and expecting "the away from home" experience at home. Enter DRONEDEK. DRONEDEK docking brings so many features and benefits to the user experience all while delivering more. In addition to the demands mentioned above, the consumer wants their purchases now. DRONEDEK docking units are a vital component in the emerging drone delivery economy. Delivering items quicker and cheaper by way of drone, autonomous driverless vehicle or robot only solves part of the problem. If those items are not delivered to a safe, smart, secure receptacle, everything gained in the process is lost at the front door. Parcel delivery is the fastest growing segment in delivery commerce. DRONEDEK docking units alone and with multi-user systems will accelerate the timing for it to happen. Additionally, DRONEDEK docking will open other facets of delivery through autonomous vehicles. Food, beverage, and pharmaceutical delivery will all benefit through the DRONEDEK platform.

The market includes all residential and commercial street addresses in the USA. Each day over 100M items are purchased on the internet of which 91% of the e-commerce deliveries are less than 5 lbs which matches the typical drone weigh capacity and fits within the DRONEDEK docking cargo bay that measures 24 by 24 inches in diameter. The market for secured drone receptacle to receive UAVs/ AMRs, courier, and/or drone deliveries are growing exponentially as demonstrated by retail statistics showing the accelerating trend of online commerce and coupled with the even faster growth of unsecured conventional delivery theft or porch piracy. The USPS reported that 1.7M USPS packages are being stolen each day, enhancing DRONDEK's market relevance and demand for its smart secured drone delivery solution. Shippers today incur an estimated $2 per delivery costs while drone delivery is estimated to generate $1 cost saving per delivery for the logistics industry. As a result, DRONEDEK's docking for multi-user systems as a business model and smart mailbox delivers a disruptive savings to the logistics industry of $1 Billion every 11 days.

Problem Solved

The improvement and problem solved as a device for a commercial or residential application serving multiple recipients/multi-users of packages. In addition, the device and docking system provides Hot and Cold Sections drone docking station with Temperature Control and maintaining devices provide temperature control for the holding section to provide both a hot and cold holding section for multiple parcels; it can administer Ultraviolet or ozone disinfecting/ detoxing to remove infectious disease, viruses and bacteria; it provides inter-communication to other drones, UAVs/ AUVS robots and couriers delivering in the area; the docking system serves as a weather monitoring station, traffic, human and pet movement with facial recognition cameras, as well as able to tag and track for authorities; it interchanges information with providers and collects information for Big Data Collection and Networking for marketing information and data and utilizes blockchain technology; at the location of the DRONEDEK docking station, it provides flood lights, two way speakers, alarms, and flashing and colored lighting for security and communications; it accommodates a drone, a mobile unit (AMR/AUV), and courier to place the unit where it is needed or wanted; it can monitor weight and size of package and can tattoo brand packages for returns; it has an assist mechanism for robot/AUVs/AMRs assist to unload of parcels to DRONEDEK docking stations; and it has an assist for and it can provide a charging station or battery exchange to the drones and AMRs/UAVs.

Prior Art

As far as known, there are no multi-user systems for parcels using this concept and system of a DRONEDEK docking system for the lead device receiving, holding, protecting, and returning parcels. It is believed that this system is unique in its design and technologies. A novelty search revealed:

A. U.S. Pat. No. 9,840,340 was issued to O'Toole in 2017. This is a Drone docking station and delivery system. Disclosed is a drone docking station for deposit of items delivered by drone. Items may include food items, groceries, parcels and others. A secure porch, roof, window or otherwise building mounted box may be secured through to an existing edifice or may be configured to mount to an existing mailbox post. The basic elements making up the components of the box enable it to carry out efficient and secure delivery of goods to a container box located at a specific address and to securely hold those goods until they are picked-up regardless of duration weather, or otherwise. The drone dock may employ different technological devices to provide communication between the drone docking station and a drone to provide security and preservation of the delivered goods before, during and after delivery.

B. U.S. Pat. No. 10,457,421 was issued to O'Toole in 2019. Another Drone docking station and delivery system. Again, disclosed is a system and device for a drone docking station for deposit of items delivered by drone. Items may include but are not limited to food items, groceries and parcels. A secure porch, roof, window or otherwise building mounted box may be secured through to an existing edifice or may be configured to mount to an existing mailbox post and take the place of the mailbox. The basic elements making of components of the box enable it to carry out one efficient and secure delivery of goods to a container box located at a specific address, and to securely hold those good until they are picked up regardless of duration, weather, or otherwise. The drone dock may employ many different technological devices in order to provide for communication between the drone dock and a drone, security, and preservation of the delivered goods before during and after delivery.

C. U.S. Pat. No. 10,093,454 was issued to Kalyan in 2018. Shown is an Unmanned aerial vehicle payload receiving apparatus. This describes an unmanned aerial vehicle ("UAV") payload receiving apparatus that may be secured to a side of a structure, such as a human residence, and positioned such that a UAV can deliver a payload into the UAV payload receiving apparatus without the UAV having to land or navigate into an area that includes objects that could be harmed by the UAV and/or harm the UAV. The UAV payload receiving apparatus may include a plurality of securing members for securing the UAV payload receiving apparatus to the structure. A top frame is coupled to the securing members, positioned in a substantially horizontal direction when the UAV payload receiving apparatus is secured to a structure, and forms an opening of a size sufficient for a payload to pass through when the payload is released by a UAV positioned above the UAV payload receiving apparatus. The UAV payload receiving apparatus also includes a payload retainer, such as a net or bag, that is coupled to and extends in a downward direction from the top frame. The payload retainer receives and retains a payload that is placed in the UAV payload receiving apparatus.

D. U.S. Pat. No. 9,367,928 issued to Gentry et al in 2016. This shows a Multi-use UAV docking station systems and methods. Here are systems and methods for providing a series of multiuse UAV docking stations are disclosed. The docking stations can be networked with a central control and a plurality of UAVs. The docking stations can include a number of services to facilitate both UAV guidance and maintenance and community acceptance and benefits. The docking stations can include package handling facilities and can act as a final destination or as a delivery hub. The docking stations can extend the range of UAVs by providing recharging/refueling stations for the UAVs. The docking stations can also include navigational aid to guide the UAVs to the docking stations and to provide routing information from the central control. The docking stations can be incorporated into existing structures such as cell towers, light and power poles, and buildings. The docking stations can also comprise standalone structures to provide additional services to underserved areas.

E. U.S. Pat. No. 10,124,912 issued to Walsh in 2018. This is a Landing pad for unmanned aerial vehicle delivery. Described as a landing pact receives and stores packages delivered from an aerial vehicle are awaiting pickup from an aerial vehicle. The landing pad can be placed outside of a window and can contain a transmitter for sending out an identification signal via radio frequency to aid aerial vehicles in finding the landing pad. The landing pad contains a landing platform with a trapdoor that leads to a storage compartment. The trapdoor can be configured to only open when it receives a signal from an authorized aerial vehicle. The storage compartment can be accessed via a storage compartment door which can contain a locking mechanism. The storage compartment can be climate controlled. The landing pad can also have a transmitter that emits sounds to discourage animals from nesting on or near the landing pad. The landing pad can also include a solar power generator as a source of electrical energy.

F. U.S. Pat. No. 9,928,749 to issued Gil et al in 2018. These are methods for delivering a parcel to a restricted access area. Here are shown systems and methods include UAVs that serve to assist carrier personnel by reducing the physical demands of the transportation and delivery process. A UAV generally includes a UAV chassis including an upper portion, a plurality of propulsion members configured to provide lift to the UAV chassis, and a parcel carrier configured for being selectively coupled to and removed from the UAV chassis. UAV support mechanisms are utilized to load and unload parcel carriers to the UAV chassis, and the UAV lands on and takes off from the UAV support mechanism to deliver parcels to a serviceable point. The UAV includes computing entities that interface with different systems and computing entities to send and receive various types of information.

As can be observed, none of the prior art has anticipated or caused one skilled in the art of DRONEDEK docking station or autobot devices or systems with multiuser devices to see this invention by O'Toole et al. as obvious to a person skilled in the ordinary art of the industry. The device and system for an autonomous mobile robot, drone, and/or courier to deliver, hold, protect, and return parcels for multi-users in both residential and commercial applications provide an answer to the problems listed.

SUMMARY OF THE INVENTION

This invention is a device and system for an automatic robot, drone, or courier to deliver, hold, protect, and return parcels. The preferred embodiment is shown in the sketches and described herein. It is compatible with all DRONEDEK docking features and includes:

A. New, small footprint combination;
B. Nine (9) to 400 parcel capacity;
C. Add-on as needed—Scale and size to needs;
D. Is a multi belt conveyor for parcels;
E. Uses cross roller turns;
F. Can Package in Tray or by itself;
G. Is compatible with re-usable packaging;
H. Has a four-post elevator with parcel tilt;
I. Has 4-way cross points with ball or roller;
J. Utilizes a lightweight interior frame;
K. Has secure outer skin;
L. Has access panels for easy maintenance;
M. Communicates and controls by DRONEDEK docking station;
N. Can Use robotic unload/pick and place;
O. Leverages known logistics systems;
P. Can have multiple delivery/receiving;
Q. Can attach to other parcel systems; and
R. Phone/FOB/Screen pick-up;

A multi-user box or sometimes termed a Cluster box is quite simply a unit that has all the functionality of one or more DRONEDEK docking stations and at the same time features numerous or multiple pigeonholes/container spaces for safe and secure storage of items to separate and distinct users in a bulk location. It is a device and system for an autonomous mobile robotic (AMRs) delivery (quadra-pods, automated guided vehicles, ground-based pods, articulated robots, bipods, humanoids, etc.), drones, and/or couriers to deliver, hold, protect, and return parcels for multi-users in both residential and commercial applications. The larger multi-user device or system can allow access by the user to their container and its contents in a fashion similar to an automated safe deposit box or in a configuration whereby the received items would be stored and protected in a bulk, non-segregated area or zone and then retrieved and delivered to the user at a common pick-up point when requested by the user. The preferred embodiment of the device and system for an autonomous mobile robot, drone, and/or courier to deliver, hold, protect, and return parcels for multi-users in both residential and commercial applications comprising: At least one set of Chambers with series of multi-belt transfer conveyors, and a series of 90-degree roller turns and a flip chute/diverter; (b) a 4-post elevator; (c) a table sorter; and (d) a receiving door, a rest platform for parcel, and a set of communication and power controls.

Objects and Advantages

There are several objects and advantages of the device and system to Deliver, Hold, Protect, and Return Parcels for multi-users residential and commercial applications. There are currently no known drone docking stations or receivers for drone or unmanned aerial vehicle (UAV), robotic carriers—autonomous mobile robots (AMRs) or automated unmanned vehicle systems (AUVS), and/or couriers that are effective at providing the objects of this invention. The various advantages and benefits are:

| Item | Advantages |
|------|------------|
| 1 | Uses DRONEDEK Technology and Features; |
| 2 | Leverage known logistics systems; |
| 3 | New, small footprint Combination; |
| 4 | Scale and size to needs; |
| 5 | Add-on new features and options as needed or desired; |
| 6 | Multiple delivery and Receiving stations; and |
| 7 | Can combine with conventional parcel systems. |

Finally, other advantages and additional features of the present device and system to Deliver, Hold, Protect, and Receive Parcels for multi-users residential and Commercial applications will be more apparent from the accompanying drawings and from the full description of the device. For one skilled in the art of drone docking stations and delivery receptacles, it is readily understood that the features shown in the examples with this product are readily adapted to other types of drone docking stations and systems and devices interfacing with drone, unmanned aerial vehicle (UAV), robotic carriers, automated unmanned vehicle systems (AUVS), and/or couriers.

DESCRIPTION OF THE DRAWINGS

Figures

The accompanying drawings, which are incorporated in and constitute a part of this specification, illustrate an embodiment of a device and system with a DRONEDEK docking system for an autonomous mobile robot (quadra-pods, automated guided vehicles, ground based pods, articulated robots, bipods, humanoids, etc.), drones, and/or courier to deliver, hold, protect, and return parcels for multi-users in both residential and commercial applications for various applications device that is preferred. The drawings together with the summary description given above and a detailed description given below explain the principles of the device and system. It is understood, however, that the device and system are not limited to only the precise arrangements and instrumentalities shown.

FIGS. 1 A through 1 C are tables of the uses, advantages, and system features of the device and system to Deliver, Hold, Protect, and Receive Parcels for multi-users residential and commercial applications—multi-user system a/k/a Cluster Box.

DESCRIPTION OF THE DRAWINGS

Reference Numerals

Figure 2:
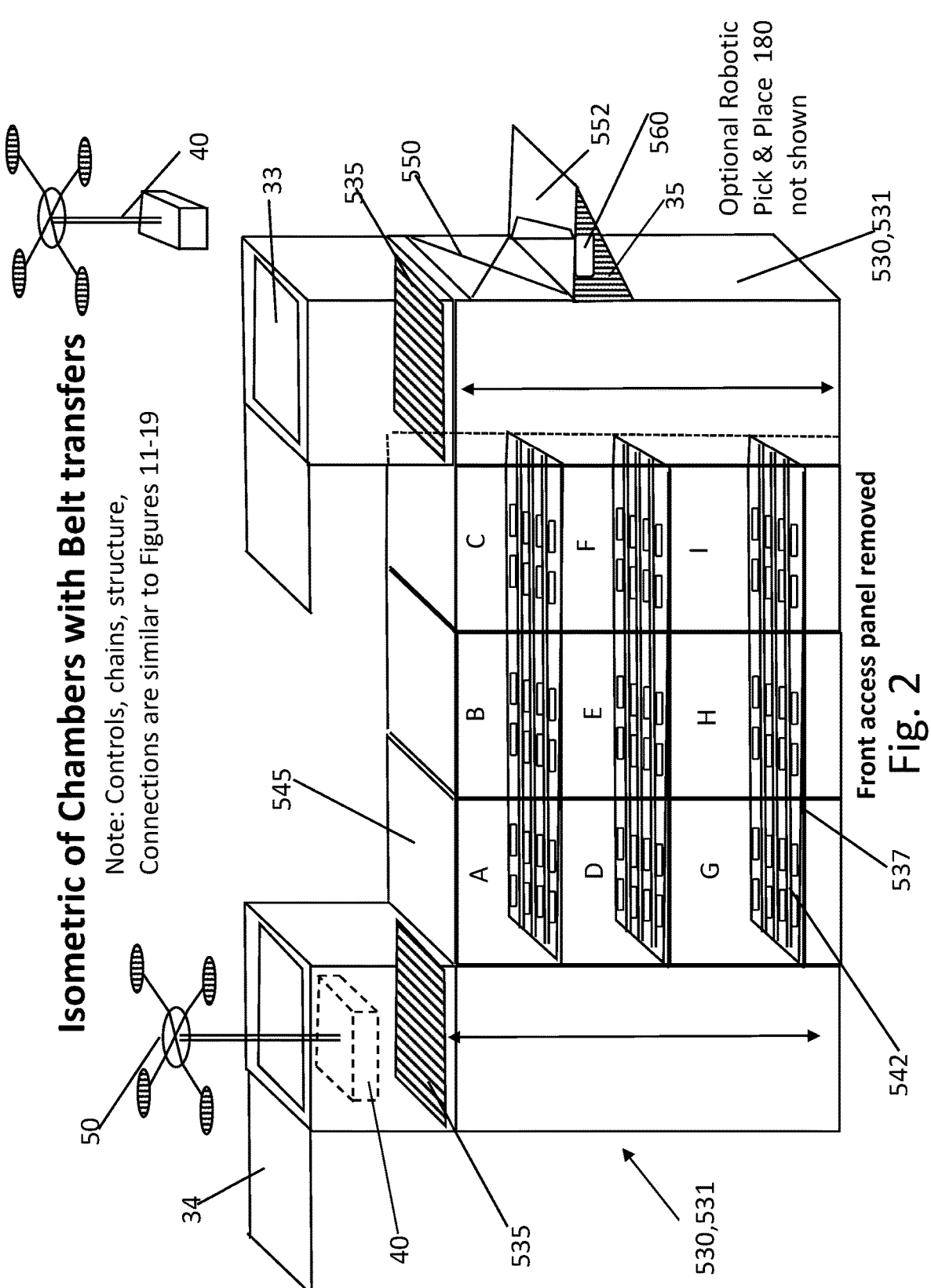
FIG. 2 is an isometric sketch of a multi-user system with a Belt transfer system and chambers.

The following list refers to the drawings:

TABLE B

| No. | Description |
|---|---|
| 30 | drone docking system/DRONEDEK 30 for deposit of items delivered by drone 50 |
| 32 | drone docking station structure 32 |
| 32A | side and side surface 32A of structure 32 |
| 32B | end and end surface 32B of structure 32 |
| 32C | bottom and bottom surface 32C of structure 32 |
| 32D | control console 32D |
| 32E | clearance 32E for slidable door 34 |
| 32F | raiseable floor 32F of enclosed structure 32 |
| 32FM | motor 32FM to lower floor 32F |
| 32DD | means 32DD to drive floor 32F chain, cable, belt, or the like |
| 32P | pulley/sprocket 32P for means 32DD |
| 32DM | means 32DM to support drive floor 32F at the end where drive means 32DD - enclosed channel, angle with castors or the like |
| 32EM | means 32EM to support drive floor 32F at opposite end of drive - enclosed channel, angle with castors or the like |
| 33 | drone structure/container opening 33 |
| 34 | closeable and openable, movable/motorized sliding or hinged/pivoting doors 34 on the dock structure 32 |
| 34A | door motor 34A |
| 35 | a means 35 for supporting the shelf 552 platform |
| 36 | a means 36 to prevent damage and deterioration like a foam or soft padding, a curved side, a sealed door, a temperature-controlled interior, and a heated sliding door. |
| 38 | top surface 38 of docking structure 32 surrounding the perimeter of the opening 34 |
| 39A | mounting pad/foundation plate 39A for structure 32 |
| 40 | parcels 40 such as food items, groceries, tools, electronics, documents, and the like |
| 50 | drone 50 |
| 50A | drone 50A with parcel |
| 50B | drone 50B empty/without parcel |
| 51 | drone pads 51 |
| 61 | camera system 61 internal/external to compartment of drone 50 having technology and recognition precision to interconnect to applications for facial recognition of humans and pets |
| 62 | optional receiving dimples 62 for the drone pads 51 |
| 63 | a means of transferring 63 the contents/parcel 40 of the drone 50 to the interior of the box through the opening 34 and a mean of disengaging from the parcel 40 such as controllable arms 64; |

TABLE B-continued

| No. | Description |
|---|---|
| | releasable/locking ball and socket with the package 65; magnetic or electronic holding structure 66 |
| 64 | controllable catch arms 64 or the like |
| 65 | releasable/locking ball and socket with the package 65 or the like |
| 66 | control system 66 for the motors 34A, 32FM, 132FM, and 232FM and interface to keyboard 116 |
| 67 | power source 67 |
| 68 | solar panel 68 as a power source |
| 69 | one or more lighting mechanisms 69 inside the container 32 |
| 70 | a means of preserving and securely storing 70 the delivered goods once in the box - i.e., a totally secure solution for home or office drone deliveries of parcels 40 |
| 71 | means for locking 71, a keypad 71A for onsite access to the DRONEDEK, facial recognition or fingerprint |
| 71A | a keypad 71A for onsite access to the DRONEDEK |
| 72 | temperature control 72 hot/cold system |
| 73 | barcode reader 73 - infrared or other |
| 73A | barcode reader waves and signals 73A |
| 73B | barcode reader label 73B on package 40 |
| 74 | wind block 74 |
| 76 | charging station 76 |
| 77 | heated top 77 |
| 78 | a motion flood light 78 that has focus technology to flood an area or create spotlight floods at specific line of sight areas in the yard near the DRONEDEK 131 |
| 79 | mail slot 79 for regular land mail |
| 80 | collector panel 80 for detection of explosives or anthrax or other perceived threats |
| 81 | battery exchange mechanism 81 for interchangeability of drone batteries with the DRONEDEK |
| 82 | extendable/retractable means for exchanging 82 batteries such as an extendable arm and securing latch to remove the drone battery 83, move it to the exchange mechanism 81 and move charged battery 84 back to drone 50 and re-engage the drone power connection |
| 83 | drone battery 83 |
| 84 | charged battery 84 |
| 85 | discharged battery 85 |
| 90 | parcel order mechanism 90 - personal communication devices 106 connected to the network 103 |
| 91 | providing system 91 or goods source - order, supplier, and distribution company - "good stuff company". |
| 92 | external lighting 92 that can be LED type systems to strobe, flash colors, communicate to authorities, distress, etc. |
| 93 | weight and dimension sensors 93 |
| 94 | two-way speakers and loud audio alarm system 94 to communicate to persons at the DRONEDEK 131 or to provide loud alarms, shrill sirens etc. |
| 100 | location and tracking means 100 of all nearby drones and communication with docking station 131 |
| 102 | a means of locating 102 the docking station 131 such that drone can approach and dock with it. GPS system or the like, etc. |
| 103 | cloud/network 103 |
| 104 | satellites 104 |
| 105 | signal and cell towers 105 |
| 106 | personal communication devices 106 - such as smart phones, tablets, laptops, personal computers, and the like |
| 107 | specific GPS address 107 for the docking station 131 |
| 108 | local signal/or mechanical means 108 - to facilitate final location and transfer such as Cold beam technology, Laser beam, Radar, Lidar, Quick Response (QR) code tags, Radio frequency RFID) remote identification tracking and sensing for drone authentication and landing for |

TABLE B-continued

Reference numbers.

| No. | Description |
| --- | --- |
|  | navigating the drone 50 to its exact location on the docking station 131 |
| 109 | encrypted signal 109 from the docking station 131 |
| 110 | a means for encrypted communication 110 between the drone and the drone dock, either directly or through a remote server (Wi-Fi, Bluetooth, hot spot, satellite etc. and others) |
| 111 | smart phone application 111 or the like to communicate status of the docking event with the user of the personal communication devices 106 |
| 112 | flight 112 from goods source 91 to docking station 131 |
| 113 | flight 113 from docking station 131 back to good source or another user destination |
| 114 | alternative flight 114 from original docking station to secondary docking station to "pick-up" parcel |
| 115 | Return tattoo printer 115 branding of package for return and ability to place gate code 115A to a codex or manual intervention and delivery |
| 116 | console control keyboard 116 |
| 117 | encrypted anti-theft chips 117 mounted to the frame |
| 120 | micro weather station 120 mechanisms, sensors, etc. |
| 122 | Paint/tag and track 122 monitoring communications and follow with GPS once painted |
| 125 | ultraviolet detox/disinfect 125 |
| 130 | ozone detox/disinfect unit 130 |
| 131 | drone docking station/DRONEDEK 131 for deposit of items delivered by drone hereinafter referred to as Special Hot and Cold Section drone docking station called a DRONEDEK Temperature Controlled, drone dock, docking station, the box, or drone box for the deposit of items delivered by drone |
| 131P | Prototype 131P of hot/cold DRONEDEK 131 |
| 131DS | design sketches 131DS of DRONEDEK with hot drawer enclosures |
| 132E | enclosure 132E for side movement of hot drawer system 234 of structure 32 in hot/cold DRONEDEK 131 |
| 132SF | solid floor 132SF of rollout section |
| 132B | bracing structure 132B for enclosure 132E for side movement |
| 132DD | means 132DD to drive floor 132F chain, cable, belt, or the like |
| 132P | pulley/sprocket 132P for means 132DD |
| 132FM | motor 132FM to raise/lower floor 132F |
| 32DD | means 132DD to drive floor 132F chain, cable, belt, or the like |
| 132P | pulley/sprocket 132P for means 132DD |
| 132DM | means 132DM to support drive floor 132F at the end where drive means 132DD - enclosed channel, angle with castors or the like |
| 132EM | means 132EM to support drive floor 132F at opposite end of drive - enclosed channel, angle with castors or the like |
| 159 | power source 159 |
| 160 | powered hot/cold plate temperature assist 160 |
| 170 | powered rollers 170 for assist platform 172 |
| 172 | assist platform 172 |
| 175 | extending support arms 175 |
| 177 | extension cylinder 177 for robot/AUVSI assist unit 180 |
| 178 | receptacles 178 for 110 V source, for cellphone charging, and for Tesla, electric scooter, and the like charging; and power source 179 for powered rollers and for Tesla, and scooter charging 178 and the like |
| 179 | power source 179 for powered rollers and for Tesla, and scooter charging 178 and the like |
| 180 | robot/AUVS (automated unmanned vehicle systems) assist unit 180 to assist unload of parcels 40 to DRONEDEK 131 |
| 190 | pick-up truck bed 190 |
| 193 | heavy duty trailer hitch support shelf 193 |
| 195 | trailer 195 - utility, dual wheel, or the like |

TABLE B-continued

Reference numbers.

| No. | Description |
| --- | --- |
| 199 | Mobile application 199 for a Special Hot and Cold Section drone docking station called a DRONEDEK Temperature Controlled |
| 232R | rails 132R that hold hot drawer system 234 as it shuttles back and forth into enclosure 132E for side movement of hot drawer |
| 232FM | motor 232FM to shuttle hot drawer system 234 |
| 234 | hot drawer system 234 that shuttles back and forth into enclosure 132E for side movement of hot drawer floor 132FS |
| 236 | means 236 to drive hot drawer system 234 back and forth on rails 232R chain, cable, belt, or the like to motor 232FM and castors along hot drawer system 234 that move along rails 232R |
| 332FM | motor and hydraulic unit 332FM to robot/AUVSI assist unit 180 |
| 400 | prior Art 400 U.S. Pat. No. 9,840,340 to O'Toole in 2017 |
| 401 | prior Art 401 U.S. Pat. No. 10,457,421 to O'Toole in 2019 |
| 402 | prior Art 402 U.S. Pat. No. 10,093,454 to Kalyan in 2018 |
| 403 | prior Art 403 U.S. Pat. No. 9,387,928 to Gentry et al in 2016 |
| 404 | prior Art 404 U.S. Pat. No. 10,124,912 to Walsh in 2018 |
| 405 | prior Art 405 U.S. Pat. No. 9,928,749 to Gil et al in 2018 |
| 530 | a device and system 530 to Deliver, Hold, Protect, and Return Parcels for multiusers residential and commercial application |
| 531 | a Chamber with Belt transfers system 531 of the device and system 530 to Deliver, Hold, Protect, and Receive Parcels for multiusers residential and commercial application aka Cluster Box |
| 533 | a Chambers 533 with table sorter 540 Belt transfers system 531 of the device and system 530 to Deliver, Hold, Protect, and Receive Parcels for multiusers residential and commercial application aka Cluster Box |
| 534 | a structure 534 |
| 535 | a 4-post elevator 535 |
| 537 | a multi belt transfer conveyor 537 |
| 540 | a table sorter 540 |
| 542 | a 90-degree roller turn 542 |
| 545 | at least one Storage chambers 545 |
| 547 | a flip chute/diverter 547 |
| 550 | a receiving door 550 |
| 552 | a rest platform 552 for parcel 40 |
| 560 | a set 560 of communication and power controls |
| 565 | a connector shroud 565 |
| 567 | a connector conveyor and transfer mechanism 567 |
| 569 | a third-party store and retrieval system 569 |
| 570 | a table 570 of users for the receptacle device and system 530 |
| 575 | a table 575 of system features for the receptacle device and system 530 |
| 577 | a table 577 of advantages for the receptacle device and system 530 |
| 600 | Uses of the device and systems 530, 531, 533, 650, and 651 for an autonomous mobile robot, drone, and/or courier to deliver, hold, protect, and return parcels for multi-users in both residential and commercial applications. |
| 601 | Arrival Point 601 single unit residential, commercial or industrial uses needing one unit |
| 602 | Arrival Bank 602 multi-users with various users - commercial, retirement communities, medical |
| 603 | Arrival Carousel 603 used with carousels and optional multi package systems, especially tight footprints and roof tops |
| 604 | Ground Arrival Convey 604 used with unloader systems of third-party vendors |
| 650 | a device and system 650 to Deliver, Hold, Protect, and Return Parcels for multiusers residential and commercial application with top funnel/parcel directors and drop through features |

TABLE B-continued

Reference numbers.

| No. | Description |
|---|---|
| 651 | a device and system 651 to Deliver, Hold, Protect, and Return Parcels for multiusers residential and commercial application |
| 652 | funnel/parcel directors 652 features such as fold out extensions and portions of the top of the DRONEDEK docking station that can be opened to various angles and help direct the parcels for receiving or sending |
| 653 | drop through features 653 for loading through bots that literally can roll under the docking station |
| 654 | top drone landing deck 654 - with features to use the 4 post elevators 535 to traverse up and down (elevate) and with omni-directional powered Mecanum wheels or equal like a moving floor to move parcels in all directions for moving to cubicle storage bins and/or third-party systems for a locker box storage |
| 655 | bottom conveyor turntable pad 655 - with features to use the corner elevators to traverse up and down (elevate) and with omni-directional powered Mecanum wheels or equal like a moving floor to move parcels in all directions for moving to cubicle storage bins and/or third-party systems for a locker box |
| 656 | features 655 of GEN 2 Dronedek including automated hinged or sliding door, mailbox, side user door for unloading and maintenance and the orientation of curbside and back side indicated. |
| 657 | Opening for Through bot to roll under and load/unload parcels 657 |

DETAILED DESCRIPTION OF PREFERRED EMBODIMENT

The present development is a device and system to Deliver, Hold, Protect, and Receive Parcels for multi-users residential and Commercial applications for various applications. This invention relates to a device for multi-users to receive Parcels from a DRONEDEK docking station. The invention relates to drones, UAVs/AMRs, and or couriers and delivery of parcels or goods to multi-user locations. The present application relates to a delivery location for receiving a package from a vehicle—drone or unmanned aerial vehicle (UAV), robotic carriers, or automated unmanned vehicle systems (AUVS). The present disclosure relates to unmanned and drone aircraft, more specifically to landing (a drone-delivered package) and docking for unmanned UAVs/AMRs to deliver or receive goods. The embodiments of the disclosure relate to the field of aircraft/drones and unmanned vehicular/robotic delivery, to a docking device for receiving and sending/returning an article. A device for a drone docking station for deposit of items delivered by drone, robot or AUVs/AMRs, and/or couriers. Items may include but are not limited to food items, groceries, and various industrial, commercial, or residential parcels. A secure porch, roof, window or otherwise building mounted box may be secured through to an existing edifice or may be configured to mount to an existing mailbox post and/or take the place of the mailbox. The invention relates to drone, AUV/AMR, and/or courier delivery of parcels or goods.

The advantages for the device and system for an autonomous mobile robot AUV/AMR, drones, and/or courier to deliver, hold, protect, and return parcels for multi-users in both residential and commercial applications are listed above in the introduction. Succinctly the benefits are that the device:

1. Uses DRONEDEK Technology and features;
2. Leverage known logistics systems;
3. New, small footprint combination;
4. Scale and size to needs;
5. Add-on as needed;
6. Multiple delivery and Receiving stations; and
7. Can combine with conventional parcel systems.

The preferred embodiment of the device and system for an autonomous mobile robot, drone, and/or courier to deliver, hold, protect, and return parcels for multi-users in both residential and commercial applications comprising: At least one set of Chambers 545 with series of multi-belt transfer conveyors 537, and a series of 90-degree roller turns 542 and a flip chute/diverter 547; (b) a 4-post elevator 535; (c) a table sorter 540; and (d) a receiving door 550, a rest platform 552 for parcel 40, and a set 560 of communication and power controls.

There is shown in FIGS. 1-19 a complete description and operative embodiment of a device and system to Deliver, Hold, Protect, and Receive Parcels for multi-users residential and Commercial applications—a/k/a Cluster Box for various applications. In the drawings and illustrations, one notes well that the FIGS. 1-19 demonstrate the general configuration and use of this product. The various example uses are in the operation and use section, below.

The accompanying drawings, which are incorporated in and constitute a part of this specification, illustrate an embodiment of the device and system for an autonomous mobile robot AUV/AMR, drones, and/or courier to deliver, hold, protect, and return parcels for multi-users in both residential and commercial applications using a docking station called a DRONEDEK Multi-User Box. The drawings together with the summary description given above and a detailed description given below explain the principles of the device and system. It is understood, however, that the device and system to Deliver, Hold, Protect, and Return Parcels for multi-users residential and commercial applications is not limited to only the precise arrangements and instrumentalities shown. Other examples of drone docking stations and package receptacles for drone or UAV/AMR, robotic carriers, and/or couriers to be within the scope and spirit shown here.

FIGS. 1 A through 1 C are tables of the uses, advantages, and system features of a device and system for an autonomous mobile robot (quadra-pods, automated guided vehicles, ground based pods, articulated robots, bipods, humanoids, etc.), drones, and/or courier to deliver, hold, protect, and return parcels for multi-users in both residential and commercial applications using a docking station called a DRONEDEK Multi-User Box. Shown in these and other sketches are a table 575 of system features for the receptacle device and system 530; and a table 577 of advantages for the receptacle device and system 530.

FIG. 2 is an isometric sketch of a multi-user system with a Belt transfer system and chambers. Portrayed here are: a device and system 530 to Deliver, Hold, Protect, and Receive Parcels for multiusers residential and commercial application aka Cluster Box; a Chamber with Belt transfers system 531 of the device and system 530 to Deliver, Hold, Protect, and Receive Parcels for multiusers residential and commercial application aka Cluster Box; a Chambers 533 with table sorter 540 Belt transfers system 531 of the device and system 530 to Deliver, Hold, Protect, and Receive Parcels for multiusers residential and commercial application aka Cluster Box; a 4-post elevator 535; a multi belt transfer conveyor 537; a table sorter 540; a 90-degree roller turn 542; at least one Storage chambers 545; a flip chute/ diverter 547; a receiving door 550; a rest platform 552 for parcel 40; a means 36 for supporting the shelf 552 support the support a means 36 for supporting the shelf 552 support 552; a set 560 of communication and power controls; a connector shroud 565; a connector conveyor and transfer mechanism 567; a third-party store and retrieval system 569; a table 570 of users for the receptacle device and system 530.

Figure 3:
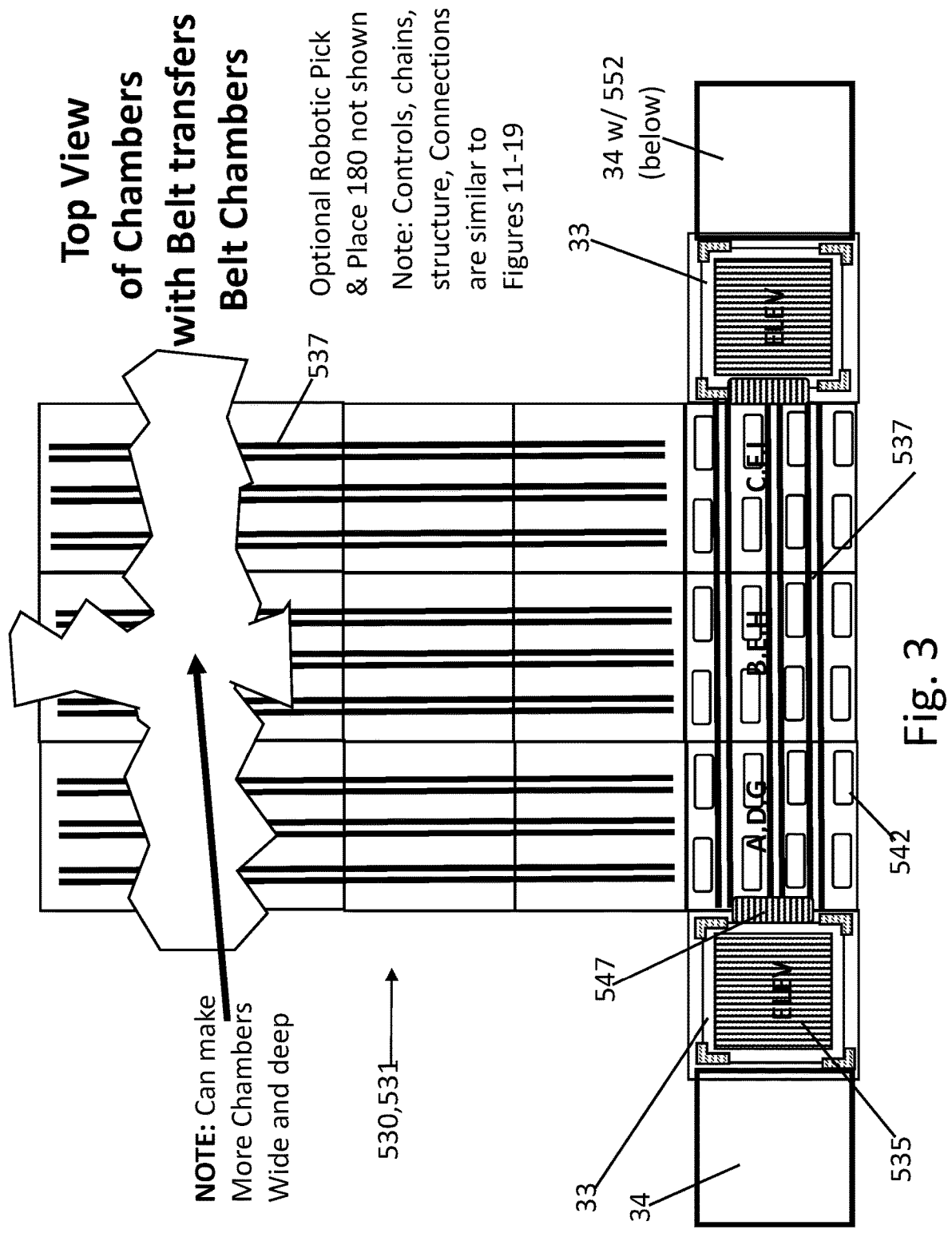
FIG. 3 is a top view of Chambers with Belt transfers. Optional Robotic Pick & Place not shown.

FIG. 3 is a top view of Chambers with Belt transfers. Optional Robotic Pick & Place not shown. Again shown are: a device and system 530 to Deliver, Hold, Protect, and Receive Parcels for multiusers residential and commercial application aka Cluster Box; a Chamber with Belt transfers system 531 of the device and system 530 to Deliver, Hold, Protect, and Receive Parcels for multiusers residential and commercial application aka Cluster Box; a Chambers 533 with table sorter 540 Belt transfers system 531 of the device and system 530 to Deliver, Hold, Protect, and Receive Parcels for multiusers residential and commercial application aka Cluster Box; a 4-post elevator 535; a multi belt transfer conveyor 537; a table sorter 540; a 90-degree roller turn 542; at least one Storage chambers 545; a flip chute/diverter 547; a receiving door 550; a rest platform 552 for parcel 40; a set 560 of communication and power controls; a connector shroud 565; a connector conveyor and transfer mechanism 567; a third-party store and retrieval system 569; a table 570 of users for the receptacle device and system 530.

Figure 4:
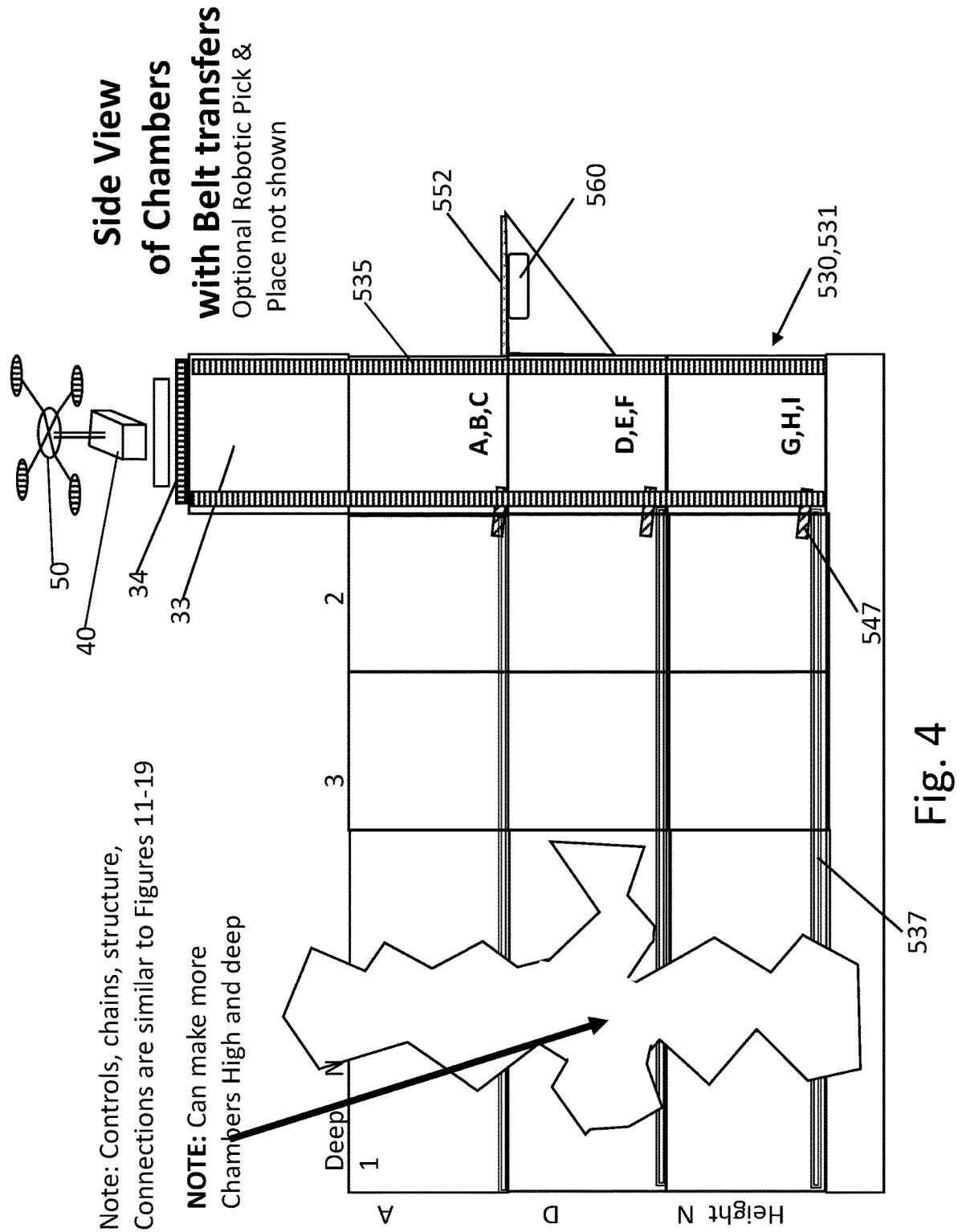
FIG. 4 is a side view of Chambers with Belt transfers. Optional Robotic Pick & Place not shown.

FIG. 4 is a side view of Chambers with Belt transfers. Optional Robotic Pick & Place not shown. Demonstrated here are: a device and system 530 to Deliver, Hold, Protect, and Receive Parcels for multiusers residential and commercial application aka Cluster Box; a Chamber with Belt transfers system 531 of the device and system 530 to Deliver, Hold, Protect, and Receive Parcels for multiusers residential and commercial application aka Cluster Box; a Chambers 533 with table sorter 540 Belt transfers system 531 of the device and system 530 to Deliver, Hold, Protect, and Receive Parcels for multiusers residential and commercial application aka Cluster Box; a 4-post elevator 535; a multi belt transfer conveyor 537; a table sorter 540; a 90-degree roller turn 542; at least one Storage chambers 545; a flip chute/diverter 547; a receiving door 550; a rest platform 552 for parcel 40; a set 560 of communication and power controls; a connector shroud 565; a connector conveyor and transfer mechanism 567; a third-party store and retrieval system 569; a table 570 of users for the receptacle device and system 530.

Figure 5:
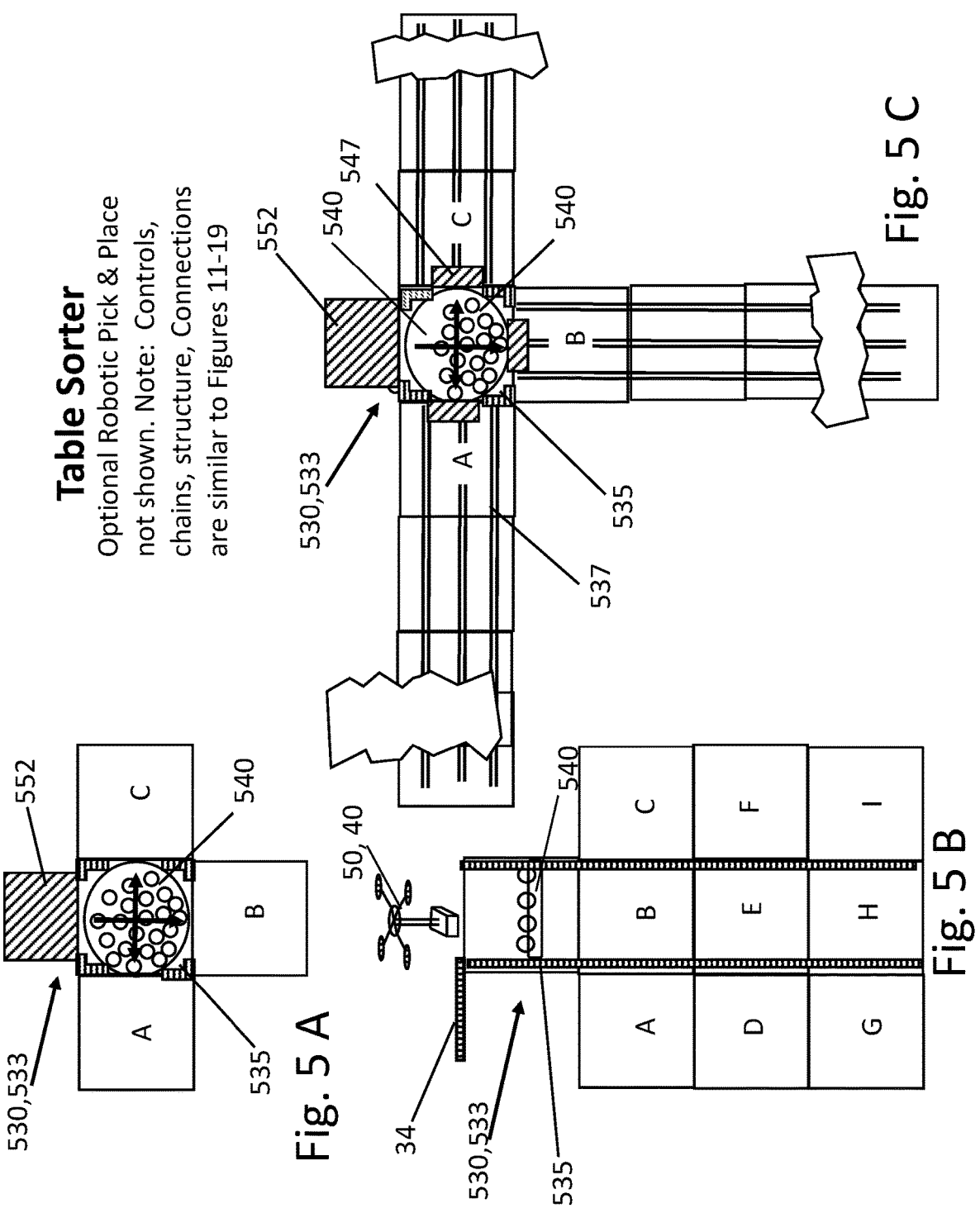
FIGS. 5 A through 5 C are top, side and end views of Chambers with a table sorter and belt transfers. Optional Robotic Pick & Place not shown.

FIGS. 5 A through 5 C are top, side and end views of Chambers with a table sorter and belt transfers. Optional Robotic Pick & Place not shown. Provided here are: a device and system 530 to Deliver, Hold, Protect, and Receive Parcels for multiusers residential and commercial application aka Cluster Box; a Chamber with Belt transfers system 531 of the device and system 530 to Deliver, Hold, Protect, and Receive Parcels for multiusers residential and commercial application aka Cluster Box; a Chambers 533 with table sorter 540 Belt transfers system 531 of the device and system 530 to Deliver, Hold, Protect, and Receive Parcels for multiusers residential and commercial application aka Cluster Box; a 4-post elevator 535; a multi belt transfer conveyor 537; a table sorter 540; a roller turn 542; at least one Storage chambers 545; a flip chute/diverter 547; a receiving door 550; a rest platform 552 for parcel 40; a set 560 of communication and power controls; a connector shroud 565; a connector conveyor and transfer mechanism 567; a third-party store and retrieval system 569; a table 570 of users for the receptacle device and system 530.

Figure 6:
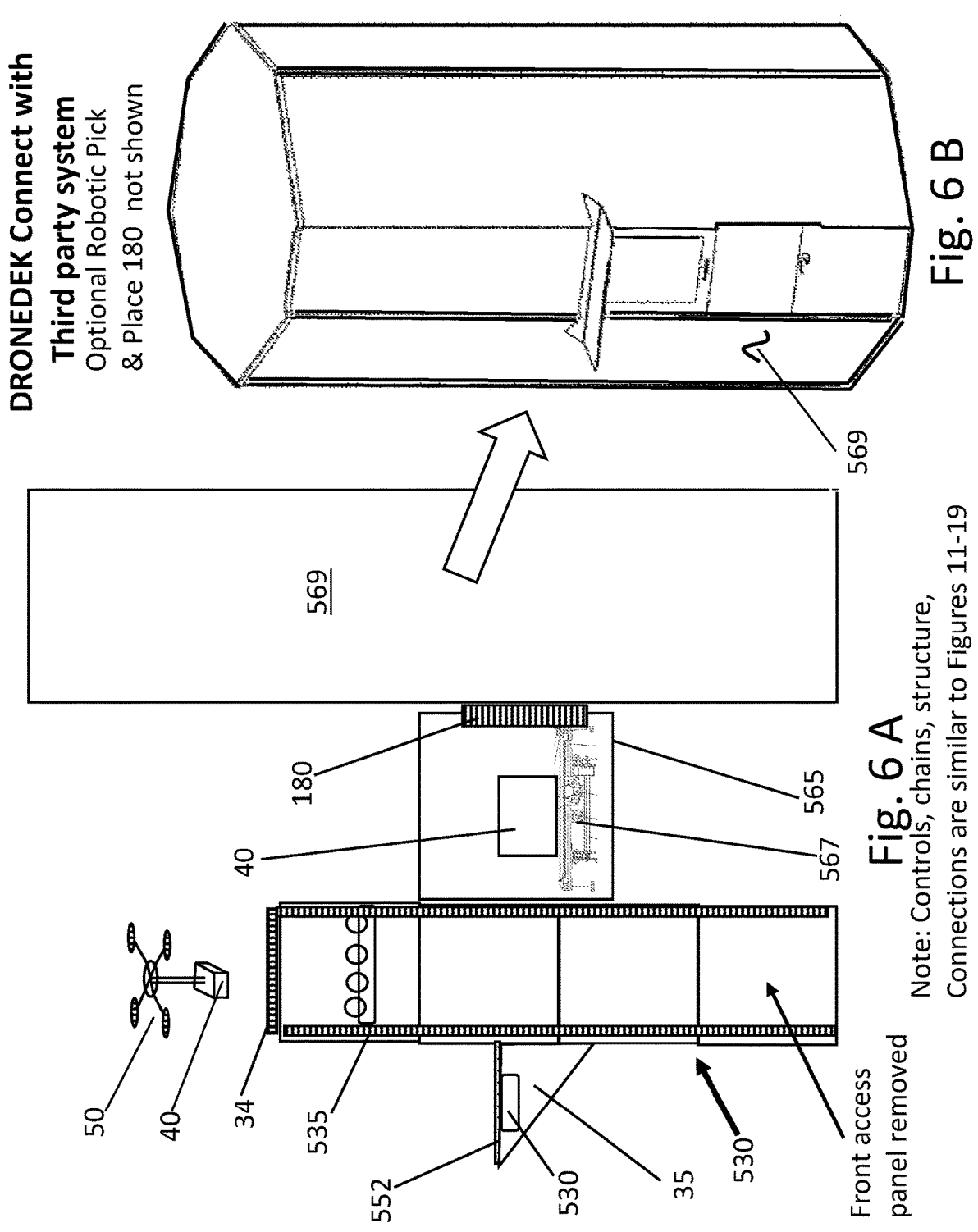
FIGS. 6 A and 6 B are views of a DRONEDEK system Connected with a Third-party parcel storage and retrieval system.

FIGS. 6 A and 6 B are views of a DRONEDEK system Connected with a Third-party parcel storage and retrieval system. Shown here are: a device and system 530 to Deliver, Hold, Protect, and Receive Parcels for multiusers residential and commercial application aka Cluster Box; a Chamber with Belt transfers system 531 of the device and system 530 to Deliver, Hold, Protect, and Receive Parcels for multiusers residential and commercial application aka Cluster Box; a Chambers 533 with table sorter 540 Belt transfers system 531 of the device and system 530 to Deliver, Hold, Protect, and Receive Parcels for multiusers residential and commercial application aka Cluster Box; a 4-post elevator 535; a multi belt transfer conveyor 537; a table sorter 540; a 90-degree roller turn 542; at least one Storage chambers 545; a flip chute/diverter 547; a receiving door 550; a rest platform 552 for parcel 40; a set 560 of communication and power controls; a connector shroud 565; a connector conveyor and transfer mechanism 567; a third-party store and retrieval system 569; a table 570 of users for the receptacle device and system 530.

Figure 7:
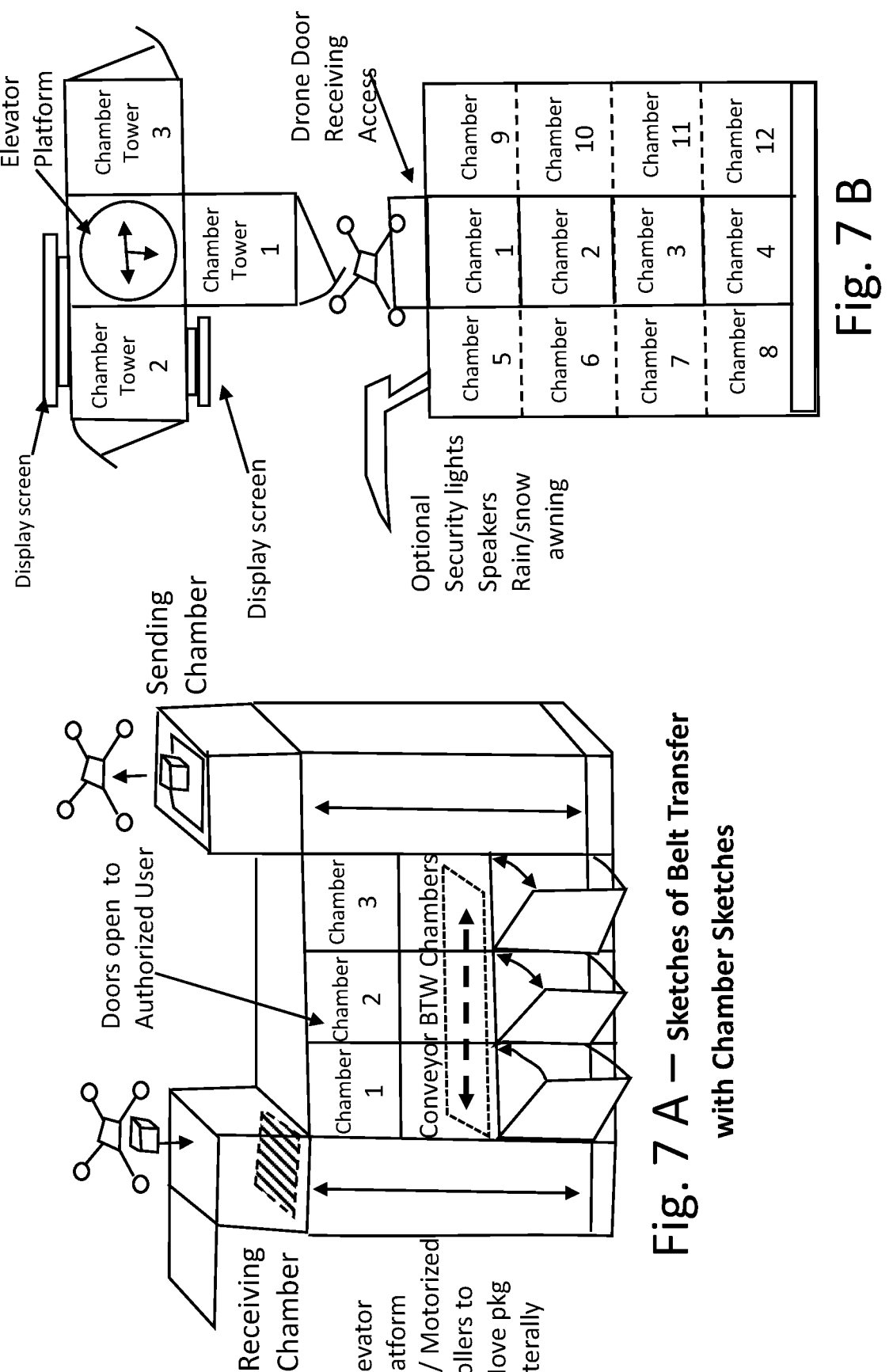
FIGS. 7 A through 7 H are views of original sketches of belt transfers and table sorter both with chamber systems, cross section views from original sketches of a belt transfer sorter with chambers, and another cross-section view and original sketch of a belt transfer sorter with chambers.
Figure 7:
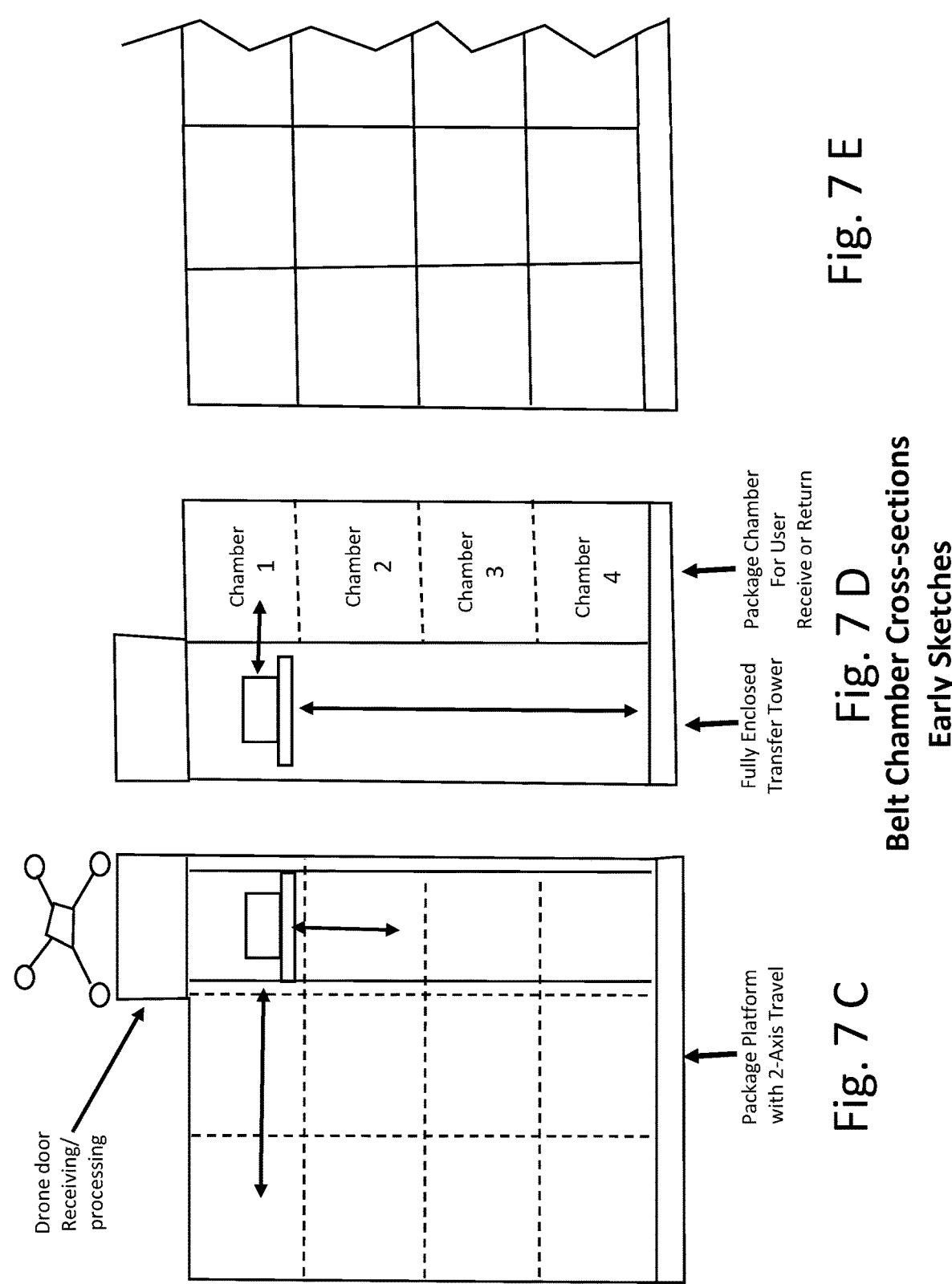
Figure 7:
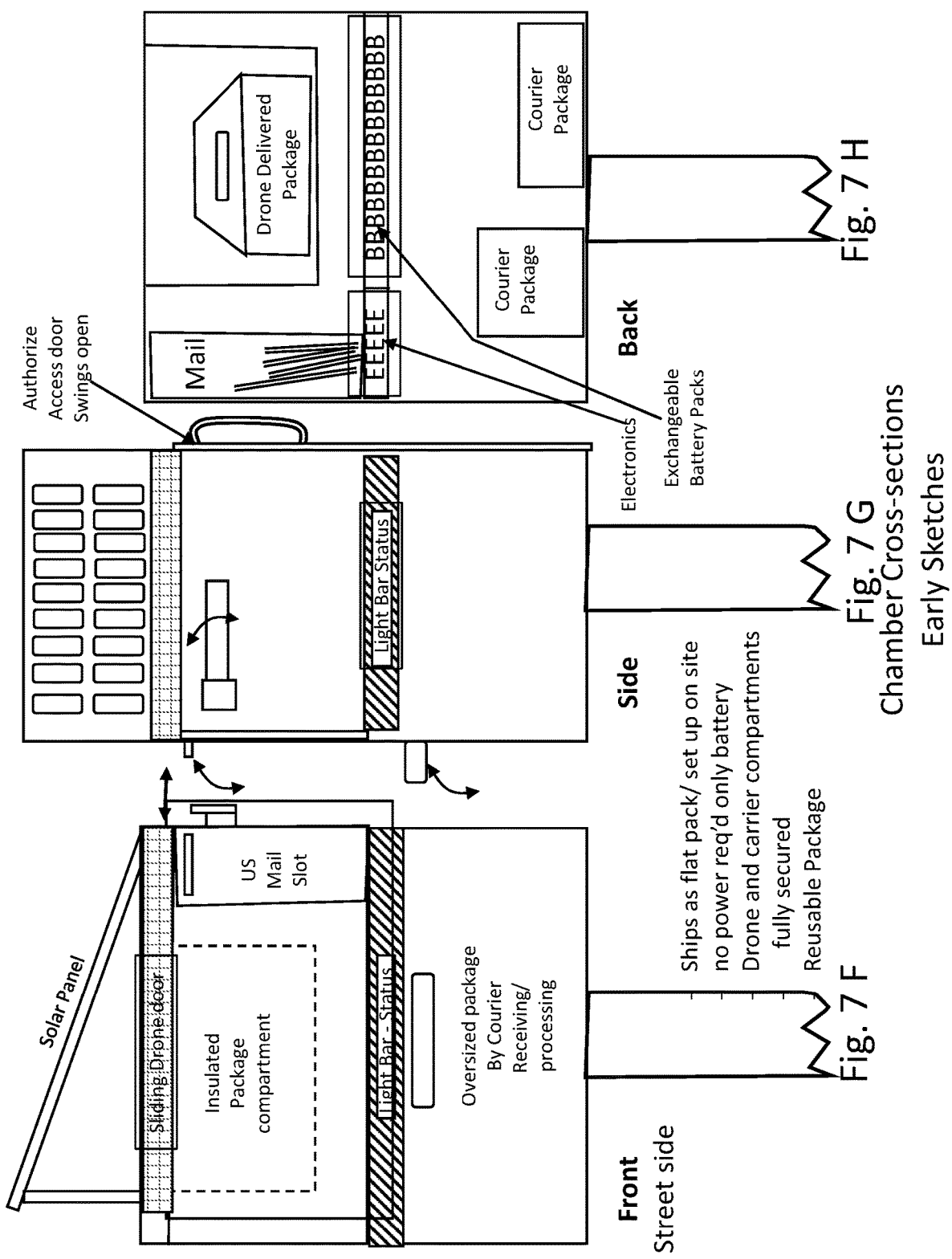

FIGS. 7 A and 7 B are views of original sketches of belt transfers and table sorter both with chamber systems. The drawings are self-explanatory, and the components are shown with the sketches in FIGS. 1 through 6, above. FIGS. 7 C through 7 E are cross section views from original sketches of a belt transfer sorter with chambers. The drawings are self-explanatory, and the components are shown with the sketches in FIGS. 1 through 6, above. FIGS. 7 F through 7 H are other cross-section views and original sketches of a belt transfer sorter with chambers. The drawings are self-explanatory, and the components are shown with the sketches in FIGS. 1 through 6, above.

Figure 8:
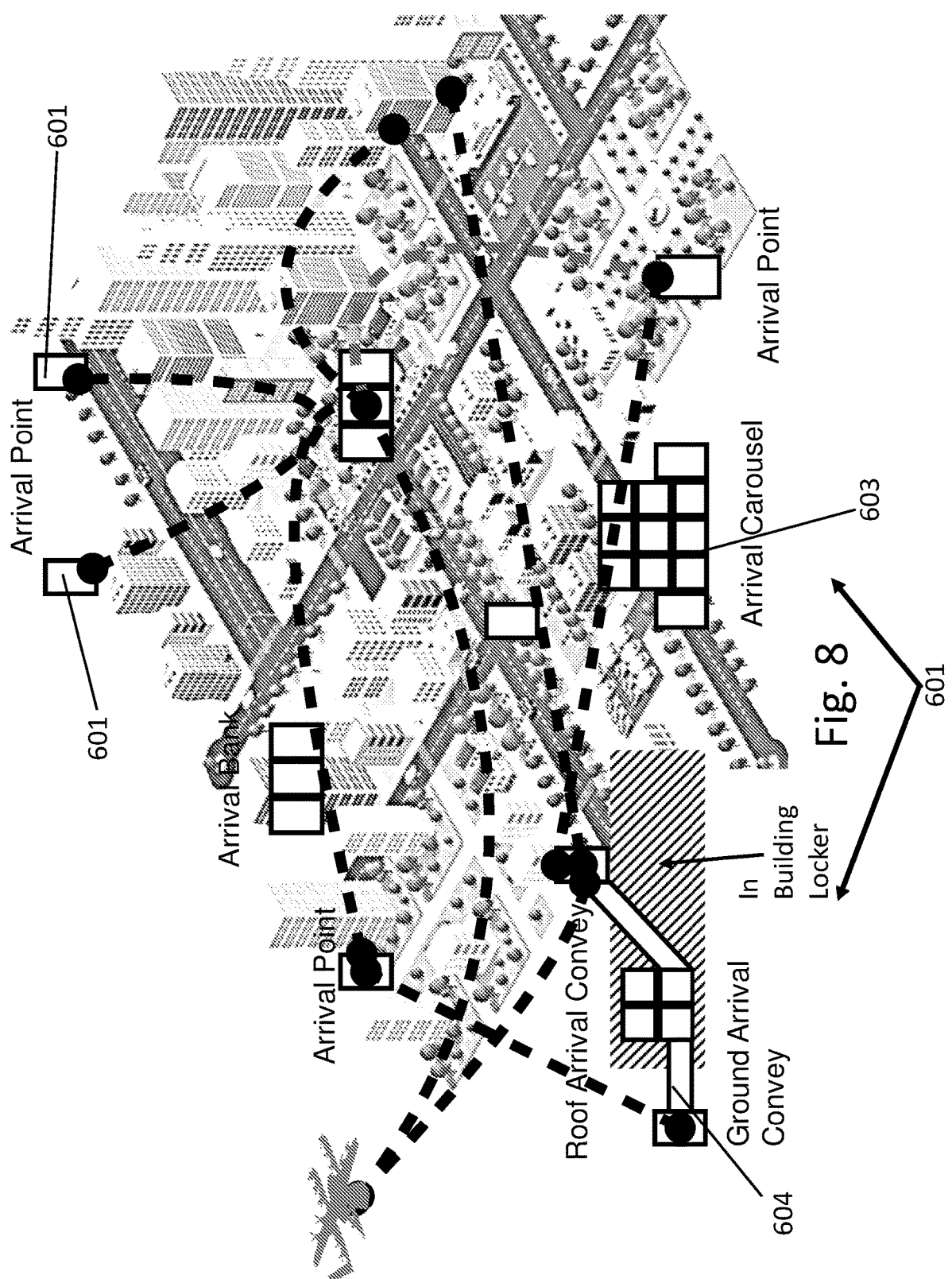
FIG. 8 is an overview of the various Autonomous Delivery Networks (ADNs) utilizing the device and system for an autonomous mobile robot, drone, and/or courier to deliver, hold, protect, and return parcels for multi-users in both residential and commercial applications.

FIG. 8 is an overview of the various Autonomous Delivery Networks (ADNs) utilizing the device and system for an autonomous mobile robot, drone, and/or courier to deliver, hold, protect, and return parcels for multi-users in both residential and commercial applications. Here are shown: Uses of the device and systems 530, 531, 533, 601, 650, and 651 for an autonomous mobile robot, drone, and/or courier to deliver, hold, protect, and return parcels for multi-users in both residential and commercial applications; Arrival Point 601 single unit residential, commercial or industrial uses needing one unit; Arrival Bank 602 multi-users with various users—commercial, retirement communities, medical; Arrival Carousel 603 used with carousels and optional multi package systems, especially tight footprints and roof tops; and Ground Arrival Convey 604 used with unloader systems of third-party vendors. This is bigger than Drones—It's about Autonomous Delivery Networks. All the major players have announced Autonomous Delivery Networks (ADN). ADN requires continuous Delivery and Pickup of varying capacities in many locations. ADN plays into DRONEDEK/Arrive's agnostic Smart Mailbox products and platform strategy. The DRONEDEK/Arrive Mailbox-as-a-Service works within various partners', retailers', Medical, and ADN business models.

Figure 9:
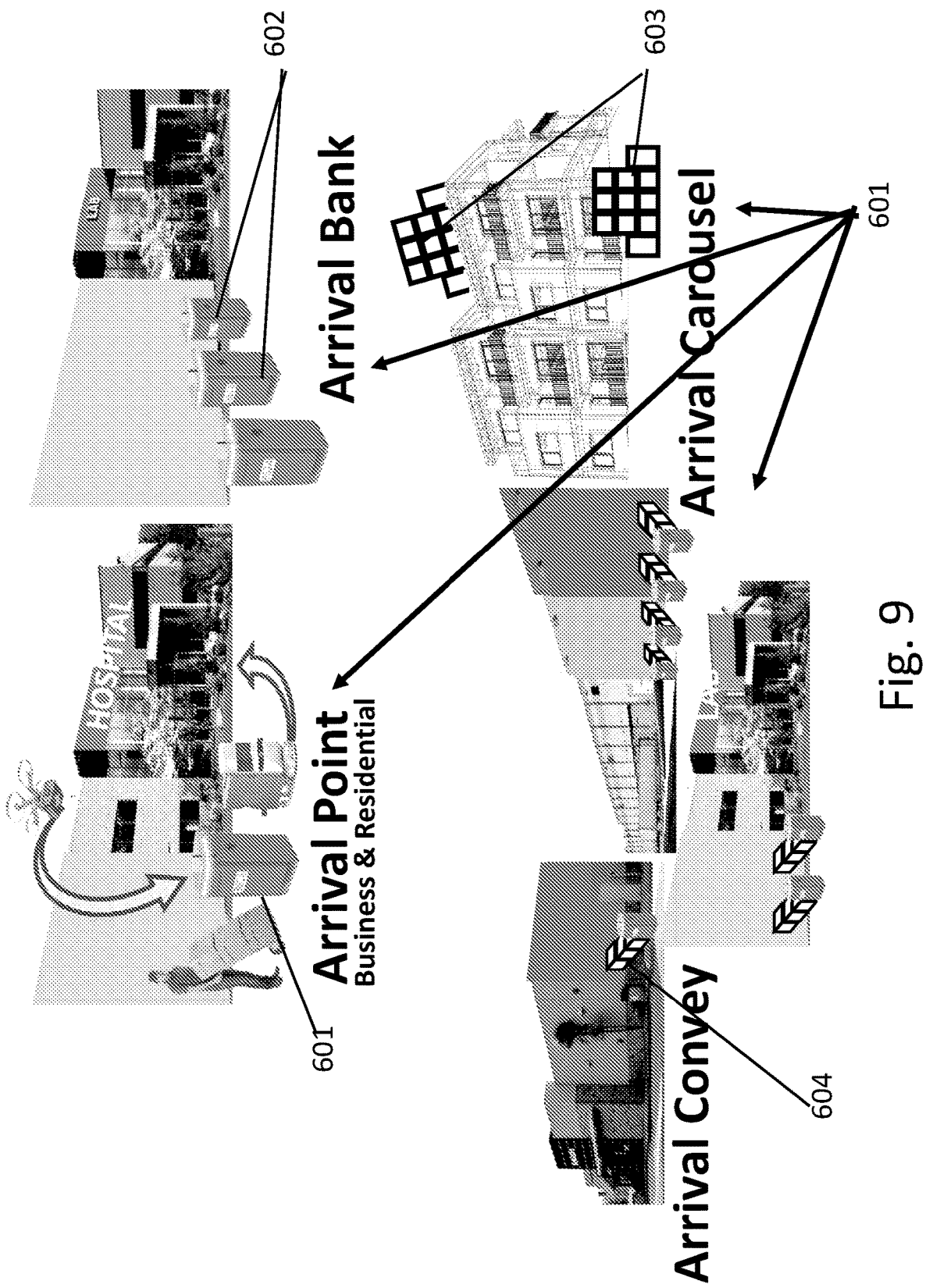
FIG. 9 are views of the ADNs and the device and system for an autonomous mobile robot, drone, and/or courier to deliver, hold, protect, and return parcels for multi-users in both residential and commercial applications.

FIG. 9 are views of the ADNs and the device and system for an autonomous mobile robot, drone, and/or courier to deliver, hold, protect, and return parcels for multi-users in both residential and commercial applications. Additional views of the uses of the device and systems 530, 531, 533, 650, and 651 for an autonomous mobile robot, drone, and/or courier to deliver, hold, protect, and return parcels for multi-users in both residential and commercial applications; Arrival Point 601 single unit residential, commercial or industrial uses needing one unit; Arrival Bank 602 multi-users with various users—commercial, retirement communities, medical; Arrival Carousel 603 used with carousels and optional multi package systems, especially tight footprints and roof tops; and Ground Arrival Convey 604 used with unloader systems of third-party vendors. Secure. This system is focused on:

Chain of Custody

Climate Assist

Smart Notifications

360 Observation

AI/ML Smart

Async Automated Delivery and Pickup

Seamless Exchanges for People, Drones, and Robotics

Cradle-to-Cradle Design.

Figure 10:
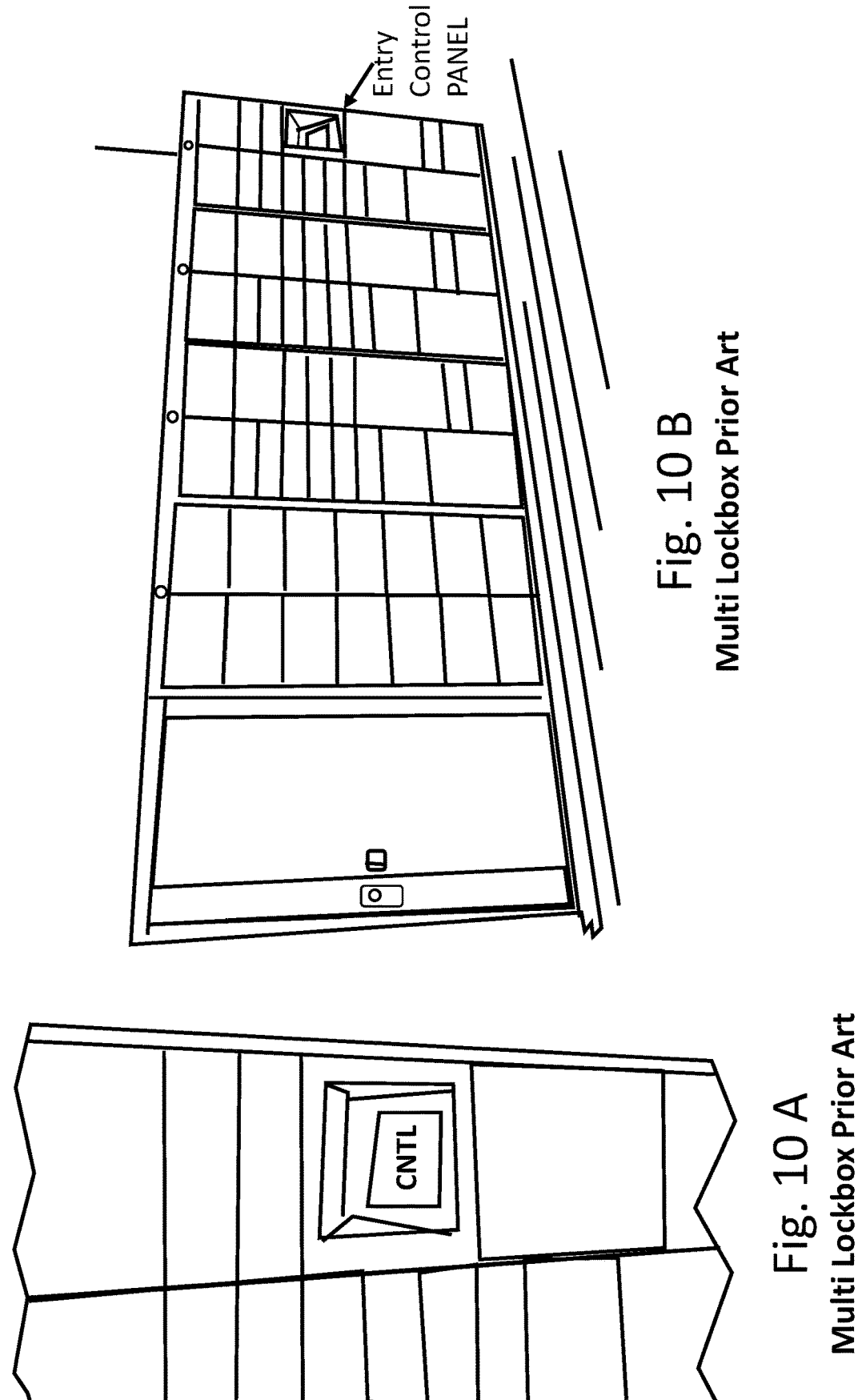
FIGS. 10 A and 10 B are typical/existing multi locker parcel holding systems.

FIGS. 10 A and 10 B are typical/prior existing multi locker parcel holding systems. The drawings are self-explanatory, and the components are shown with the sketches in FIGS. 1 through 6, above.

Figure 11:
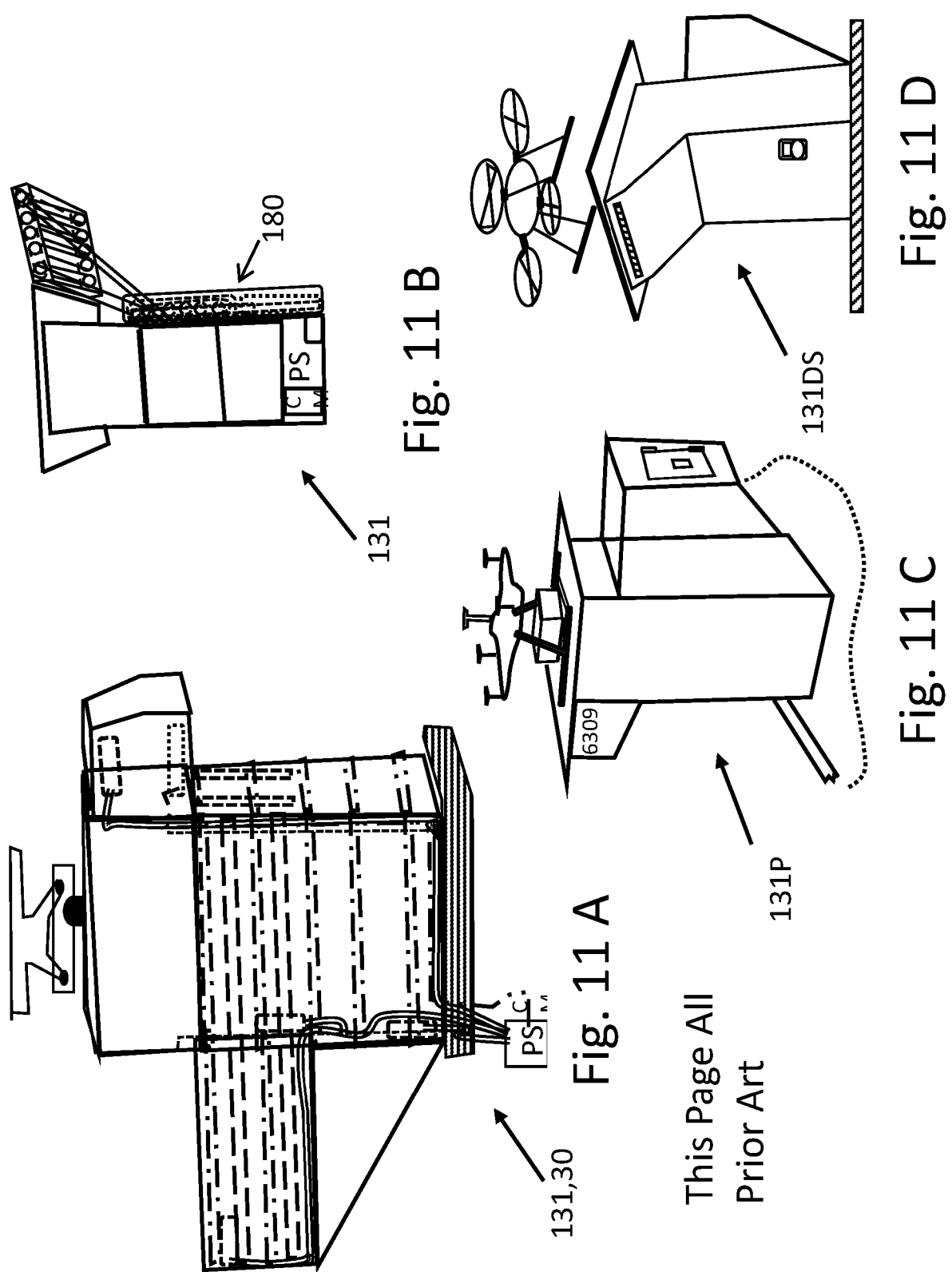
FIGS. 11 A through 11 D are sketches of the general drone docking station/DRONEDEK for deposit of items delivered by drone hereinafter referred to as Special Hot and Cold Section drone docking station called a DRONEDEK Temperature Controlled device.

FIGS. 11 A through 11 E are sketches of the general prior existing drone docking station/DRONEDEK 131 for deposit of items 40 delivered by drone 50 hereinafter referred to as Special Hot and Cold Section drone docking station called a DRONEDEK Temperature Controlled device 131. Viewed in these sketches are: a drone docking station/DRONEDEK 131 for deposit of items delivered by drone 50 hereinafter referred to as Special Hot and Cold Section drone docking station called a DRONEDEK Temperature Controlled device 131, drone dock, docking station, the box, or drone box for the deposit of items delivered by drone; a prototype 131P of DRONEDEK with Special Hot and Cold Section drone docking station called a DRONEDEK Temperature Controlled device; a design sketch 131DS of DRONEDEK with hot and cold temperature control; a Mobile application 199 for a Special Hot and Cold Section drone docking station called a DRONEDEK Temperature Controlled device 131; and a robot/AUVS (automated unmanned vehicle systems) assist unit 180 to assist unload of parcels 40 to temperature controlled sections DRONEDEK device 131.

Figure 12:
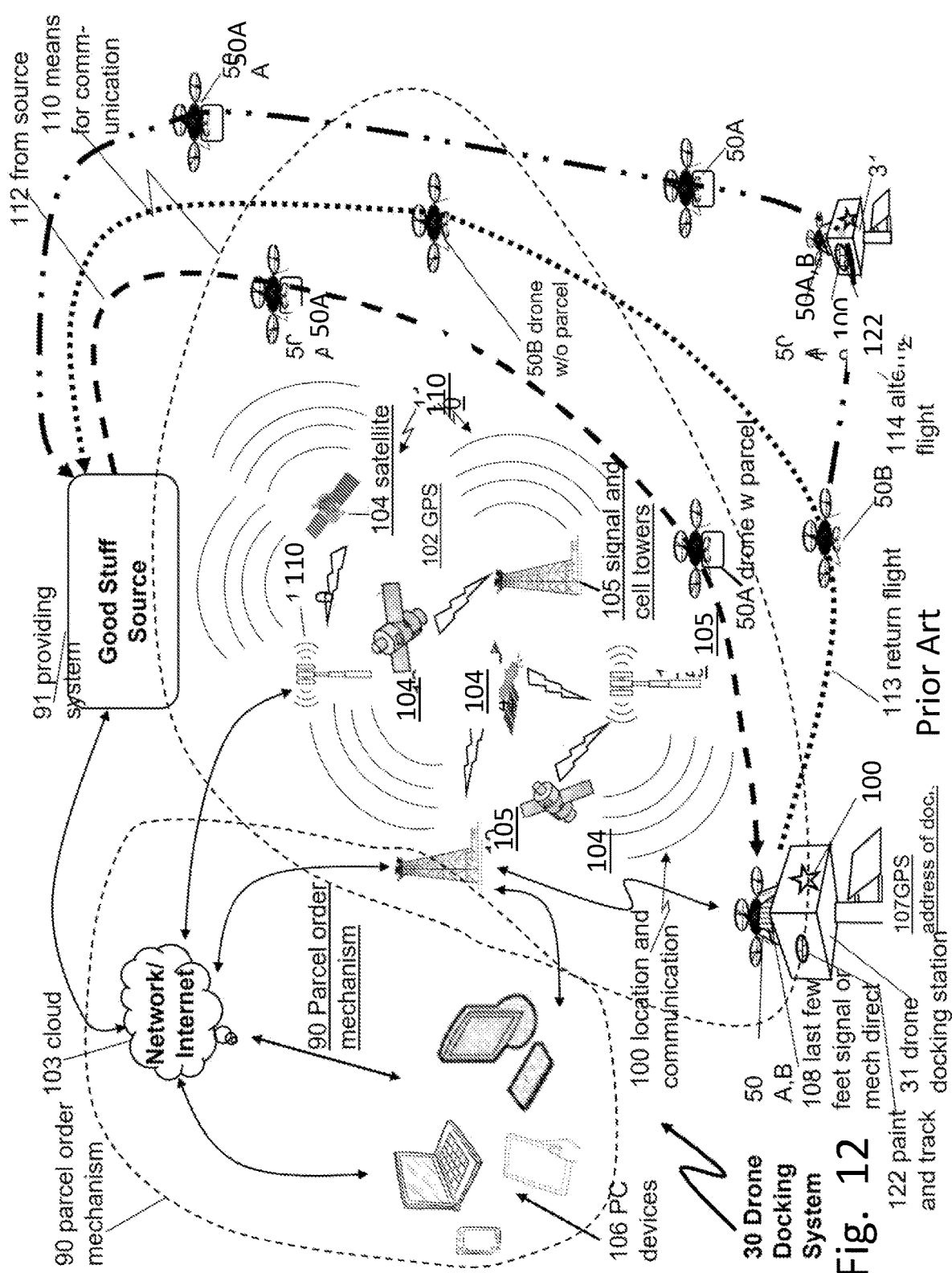
FIG. 12 shows the communication and delivery system from the order of the product/parcel to the delivery to the docking station/DRONEDEK with the hot/cold section with temperature control.

FIG. 12 shows the communication and delivery system from the order of the product/parcel to the delivery to the prior art docking station/DRONEDEK device 131 with the hot/cold section with temperature control. In this view is: drone docking station/DRONEDEK 131,30 for deposit of items delivered by drone hereinafter referred to as Special Hot and Cold Section drone docking station called a DRONEDEK Temperature Controlled Device, drone dock, docking station, the box, or drone box for the deposit of items delivered by drone; a parcel 40 such as food items, groceries, tools, electronics, documents, and the like; a drone 50; a drone 50A with parcel; a drone 50B empty/without parcel; a parcel order mechanism 90—personal communication devices 106 connected to the network 103; a providing system 91 or goods source—order, supplier, and distribution company—"good stuff company"; a location and tracking means 100 of all nearby drones and communication with docking station 131,30; a means of locating 102 the docking station 131 such that drone can approach and dock with it. GPS system or the like, etc.; a cloud/network 103; a group of satellites 104; a signal and cell towers 105; a personal communication devices 106—such as smart phones, tablets, laptops, personal computers, and the like; a specific GPS address 107 for the docking station 131; local signal/or mechanical means 108—to facilitate final location and transfer such as Cold beam technology, Laser beam, Radar, Lidar, Quick Response (QR) code tags, Radio frequency RFID) remote identification tracking and sensing for drone authentication and landing for navigating the drone 50 to its exact location on the docking station 131;

an encrypted signal 109 from the docking station 131; a means for communication 110 between the drone and the drone dock, either directly or through a remote server (Wi-Fi, Bluetooth, hot spot, satellite etc. and others); a smart phone application 111 or the like to communicate status of the docking event with the user of the personal communication devices 106; a flight 112 from goods source 91 to docking station 131; a flight 113 from docking station 131 back to good source or other user destination; an alternative flight 114 from original docking station to secondary docking station to "pick-up" parcel; and a paint/tag and track 122 monitoring communications and ability follow items with GPS once painted. In the overall control system with the Dronedek receptacles 30, 131, air traffic control data for drone "FAA"—DRONEDEK to utilize drone tracking capabilities and feature. The drone tracking and monitoring features to provide mapping of drone location in and around the geographical area of each DRONDEDEK. Like flightware the drone-ware feature to provide visibility of drones operating in the market including aerial mapping. air traffic control whereby DRONEDEK can schedule incoming and outgoing shipments and can be prioritized by user; marketplace conduit; big data metrics harvesting.

Figure 13:
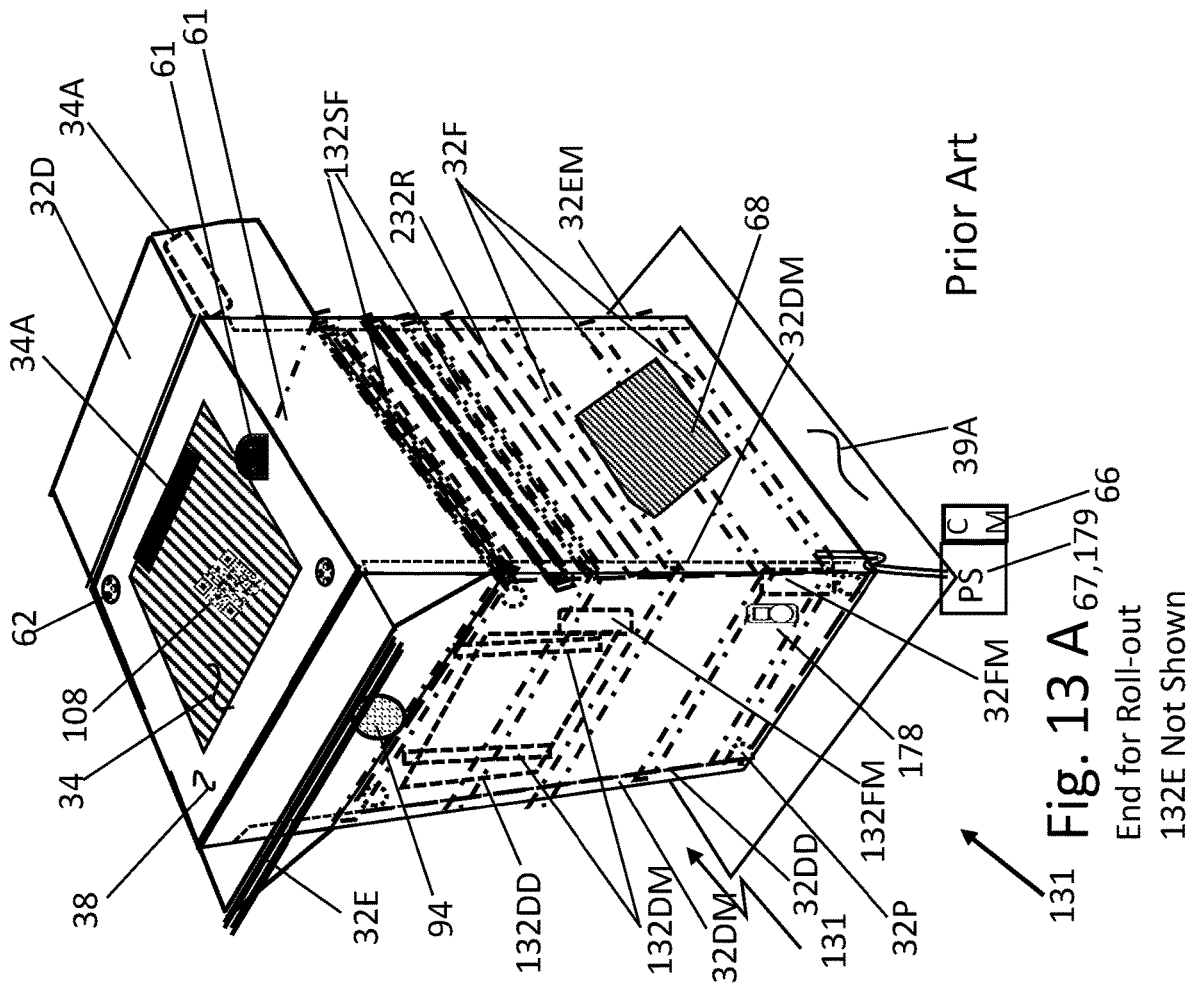
FIGS. 13 A through 13 C are sketches of a docking station/DRONEDEK with the Special Hot and Cold Section drone docking station called a DRONEDEK Temperature Controlled device with the components and features shown from generally a side or end view.
Figure 13:
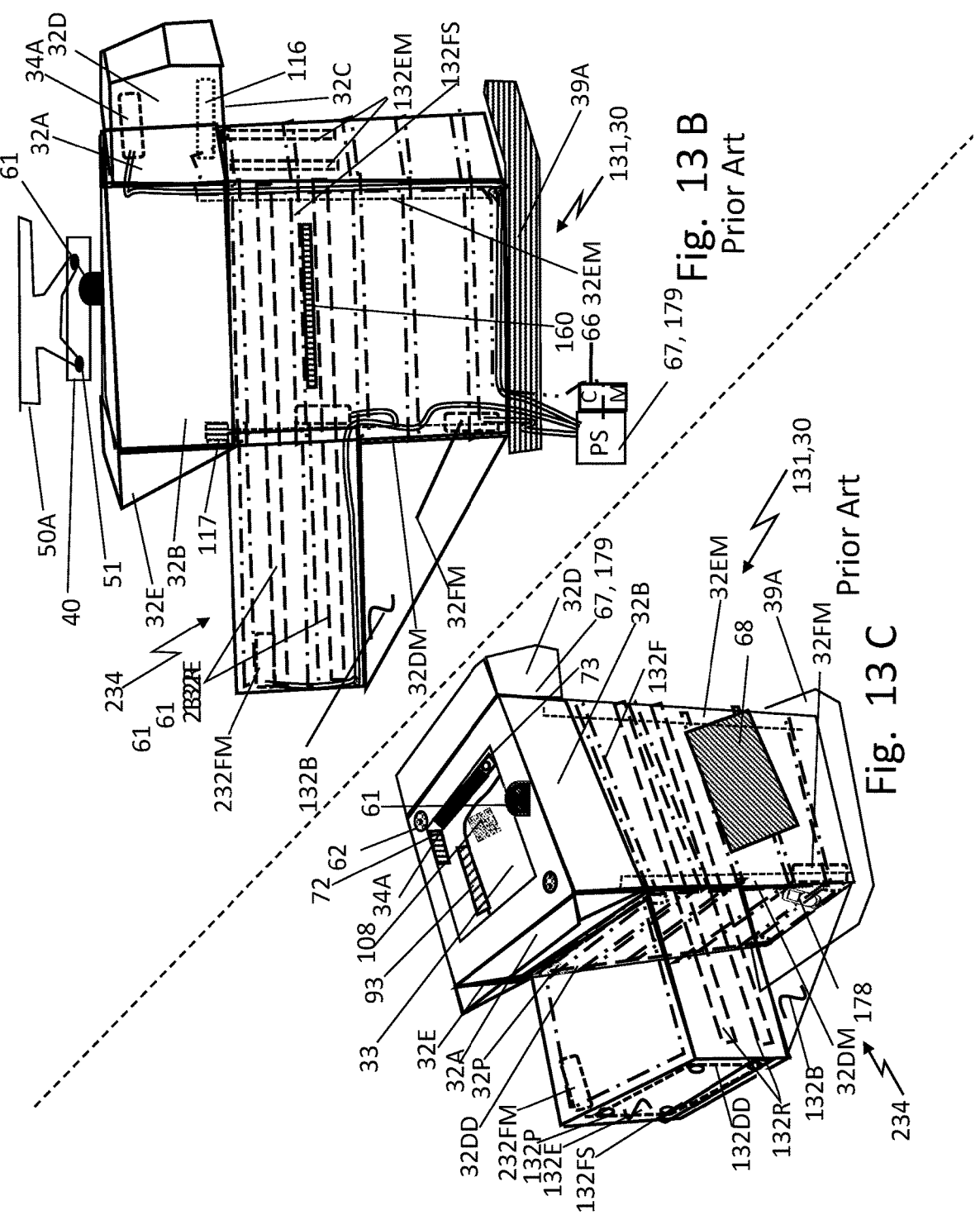

FIGS. 13 A through 13 C are sketches of a prior art docking station/DRONEDEK 131, 30 with the Special Hot and Cold Section drone docking station called a DRONEDEK Temperature Controlled device 131 with the components and features shown from generally a side or end view. These drawings portray: a drone docking station/DRONDEDEK 131 for deposit of items delivered by a drone 50 hereinafter referred to as Special Hot and Cold Section drone docking station called a DRONEDEK Temperature Controlled device 131, drone dock, docking station, the box, or drone box for the deposit of items delivered by drone; drone docking station structure 32 with a raiseable floor 32F; a side and side surface 32A of structure 32; an end and end surface 32B of structure 32; a bottom and bottom surface 32C of structure 32; a control console 32D; a clearance 32E for slidable or hinged/pivoting door 34; a raiseable floor 32F of enclosed structure 32; a motor 32FM to lower floor 32F; a means 32DD to drive floor 32F chain, cable, belt, or the like; a pulley/sprocket 32P for means 32DD; a means 32DM to support drive floor 32F at the end where drive means 32DD—enclosed channel, angle with castors or the like; a means 32EM to support drive floor 32F at opposite end of drive—enclosed channel, angle with castors or the like; a drone structure/container opening 33; a closeable and openable, movable/motorized sliding door 34 on the dock structure 32; a door motor 34A; a means 36 to prevent damage and deterioration like a foam or soft padding, a curved side, a sealed door, a temperature controlled interior, and a heated sliding door; a top surface 38 of docking structure 32 surrounding the perimeter of the opening 34; a mounting pad/foundation plate 39A for structure 32; a parcel 40 such as food items, groceries, tools, electronics, documents, and the like; a drone 50; a drone 50A with parcel; a camera system 61 internal/external to compartment of drone 50 having technology and recognition precision to interconnect to applications for facial recognition of humans and pets; an optional receiving dimples 62 for the drone pads 51; a control system 66 for the motors 34A, 32FM, 132FM, 232FM, 332FM, and interface to keyboard 116; a power source 67; a solar panel 68 as a power source; a means of preserving and securely storing 70 the delivered goods once in the box—i.e. a totally secure solution for home or office drone deliveries of parcels 40; a temperature control 72 hot/cold system; a barcode reader 73—infrared or other; a temperature control 72 hot/cold system; a barcode reader 73—infrared or other; two-way speakers and loud audio alarm system 94 to communicate to persons at the DRONEDEK 131 or to provide loud alarms, shrill sirens etc.; local signal/or mechanical means 108—to facilitate final location and transfer such as Cold beam technology, Laser beam, Radar, Lidar, Quick Response (QR) code tags, Radio frequency RFID) remote identification tracking and sensing for drone authentication and landing for navigating the drone 50 to its exact location on the docking station 31; a console control keyboard 116; an encrypted anti-theft chips 117 mounted to the frame; an enclosure 132E for side movement of hot drawer system 234 of structure 32 in hot/cold DRONEDEK 131; a solid floor 132SF of rollout section; a bracing structure 132B for enclosure 132E for side movement; a means 132DD to drive floor 132SF chain, cable, belt, or the like; a pulley/sprocket 132P for means 132DD; a motor 132FM to raise/lower floor 132F; a means 132DD to drive floor 132F chain, cable, belt or the like; a pulley/sprocket 132P for means 132DD; a means 132DM to support drive floor 132SF at the end where drive means 132DD—enclosed channel, angle with castors or the like; a means 132EM to support drive floor 132SF at opposite end of drive—enclosed channel, angle with castors or the like; a set of rails 132R that hold hot drawer system 234 as it shuttles back and forth into enclosure 132E for side movement of hot drawer; a receptacle 178 for 110 V source, for cellphone charging, and for Tesla, electric scooter, and the like charging; and power source 179 for powered rollers and for Tesla, and scooter charging 178 and the like; a power source 179 for powered rollers and for Tesla, and scooter charging 178 and the like; a motor 232FM to shuttle hot drawer system 234; a hot drawer system 234 that shuttles back and forth into enclosure 132E for side movement of hot drawer; a means 236 to drive hot drawer system 234 back and forth on a set of rails 232R chain, cable, belt or the like to motor 232FM and castors along hot drawer system 234 that move along rails 232R; and a powered hot/cold plate temperature assist 160.

Figure 14:
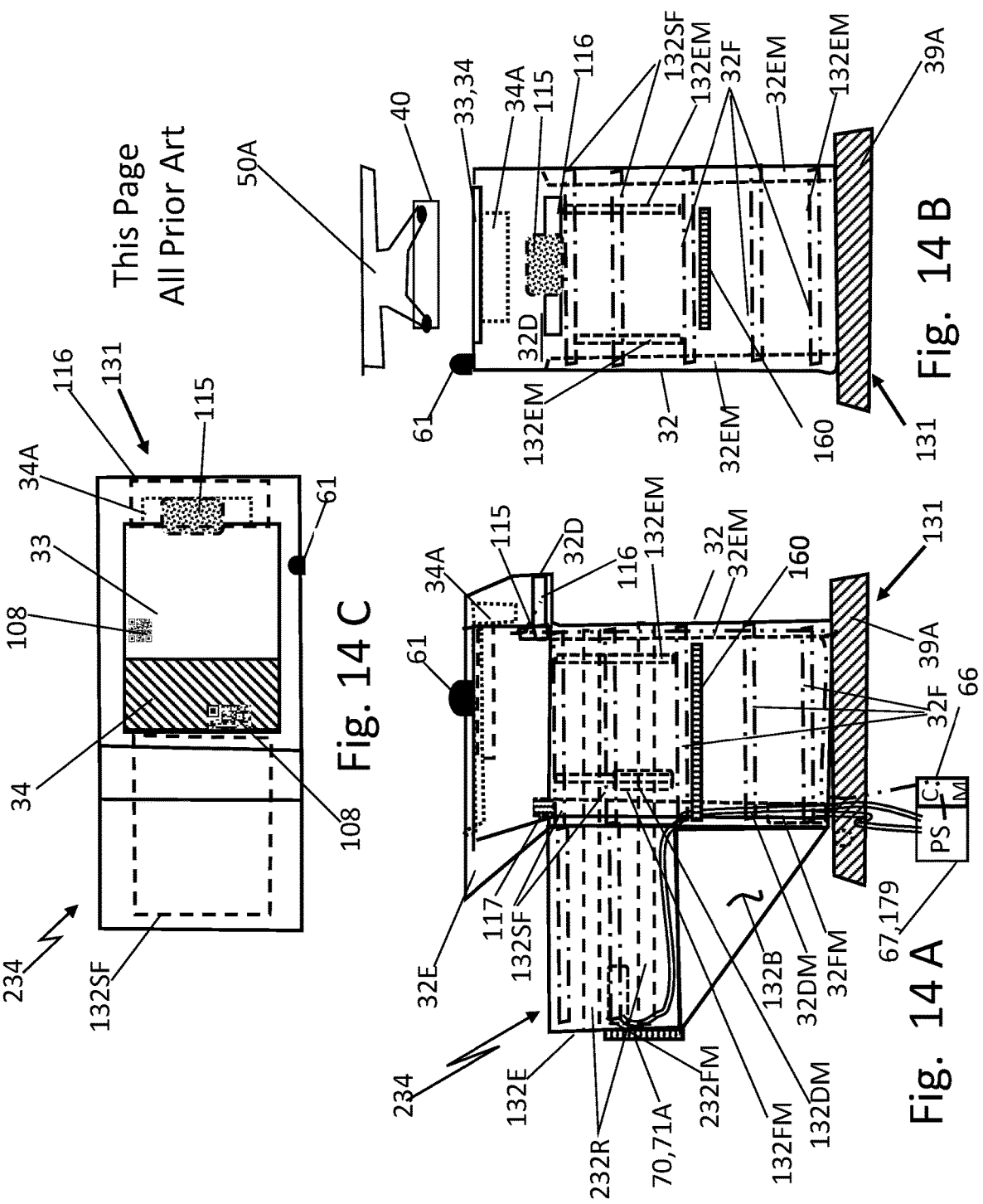
FIGS. 14 A through 14 D are more sketches of a docking station/DRONEDEK with the Special Hot and Cold Section drone docking station called a DRONEDEK Temperature Controlled device with the components and features shown from several views.
Figure 14:
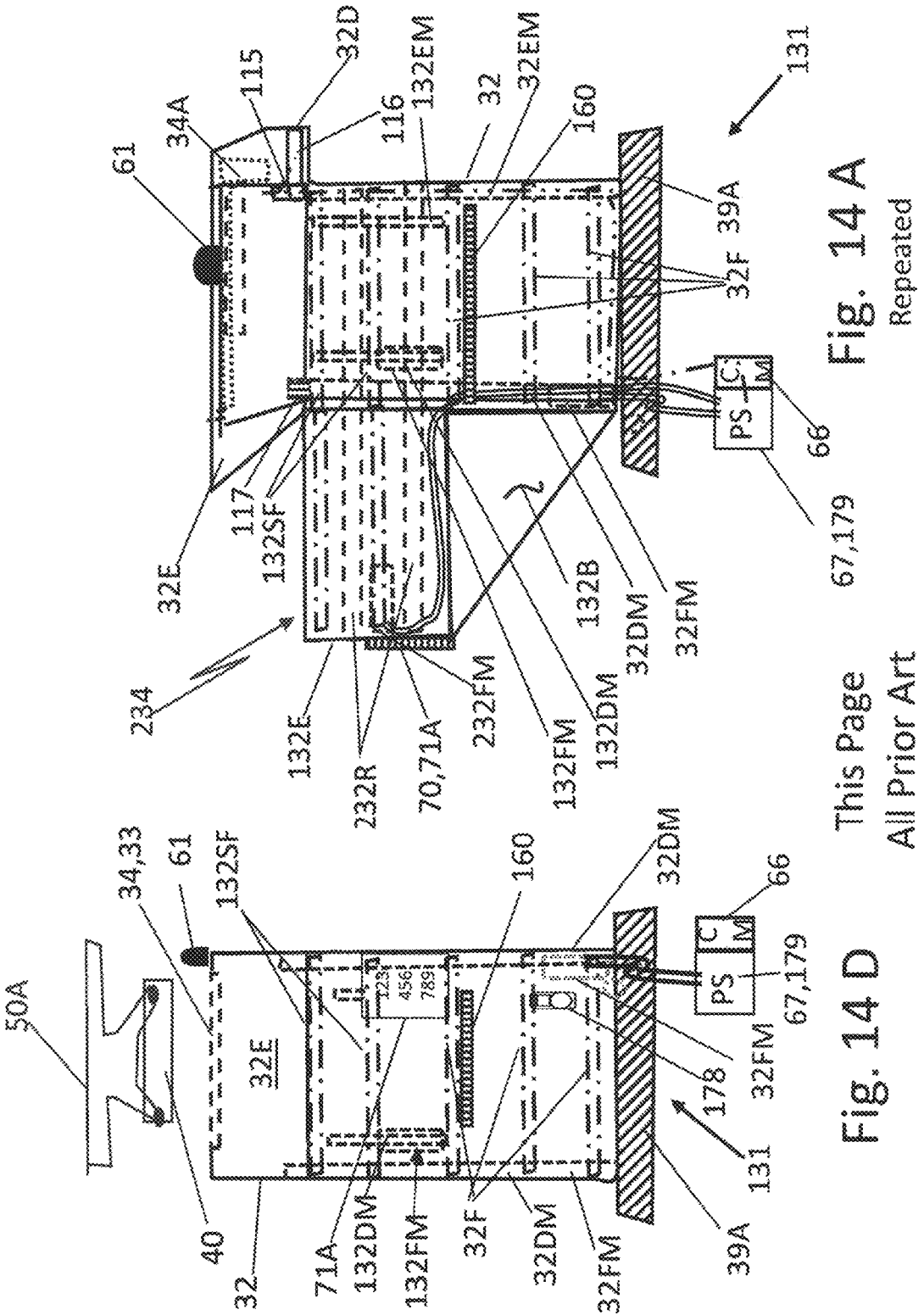

FIGS. 14 A through 14 D FIGS. are more sketches of a prior art docking station/DRONEDEK 131 with the Special Hot and Cold Section drone docking station called a DRONEDEK Temperature Controlled device 131 with the components and features shown from several views. Demonstrated in these views are: a drone docking station/ DRONEDEK 131 for deposit of items delivered by drone the station having a Special Hot and Cold Section drone docking station called a DRONEDEK Temperature Controlled device 131; drone docking station structure 32 with expanding section/accordion with a raiseable floor 32F; a side and side surface 32A of structure 32; an end and end surface 32B of structure 32; a bottom and bottom surface 32C of structure 32; a control console 32D; a clearance 32E for slidable or hinged/pivoting door 34; a raiseable floor 32F of enclosed structure 32; a motor 32FM to lower floor 32F; a means 32DD to drive floor 32F chain, cable, belt, or the like; a pulley/sprocket 32P for means 32DD; a means 32DM to support drive floor 32F at the end where drive means 32DD—enclosed channel, angle with castors or the like; a means 32EM to support drive floor 32F at opposite end of drive—enclosed channel, angle with castors or the like; a drone structure/container opening 33; a closeable and openable, movable/motorized sliding door 34 on the dock structure 32; a door motor 34A; a means 36 to prevent damage and deterioration like a foam or soft padding, a curved side, a sealed door, a temperature controlled interior, and a heated sliding door; a top surface 38 of docking structure 32 surrounding the perimeter of the opening 34; a mounting pad/foundation plate 39A for structure 32; a parcel 40 such as food items, groceries, tools, electronics, documents, and the like; a drone 50; a drone 50A with parcel; a camera system 61 internal/external to compartment of drone 50 having technology and recognition precision to interconnect to applications for facial recognition of humans and pets; an optional receiving dimples 62 for the drone pads 51; a control system 66 for the motors 34A, 32FM, 132FM, 232FM, 332FM, and interface to keyboard 116; a power source 67; a solar panel 68 as a power source; a means of preserving and securely storing 70 the delivered goods once in the box—i.e. a totally secure solution for home or office drone deliveries of parcels 40; a temperature control 72 hot/cold system; a barcode reader 73—infrared or other; a temperature control 72 hot/cold system; a barcode reader 73—infrared or other; two-way speakers and loud audio alarm system 94 to communicate to persons at the DRONEDEK 131, 131 or to provide loud alarms, shrill sirens etc.; a local signal/or mechanical means 108—to facilitate final location and transfer such as Cold beam technology, Laser beam, Radar, Lidar, Quick Response (QR) code tags, Radio frequency RFID) remote identification tracking and sensing for drone authentication and landing for navigating the drone 50 to its exact location on the docking station 31; a return tattoo printer 115 branding of package for return and ability to place gate code 115A to a codex or manual intervention and delivery; a console control keyboard 116; an encrypted anti-theft chips 117 mounted to the frame; an enclosure 132E for side movement of hot drawer system 234 of structure 32 in hot/cold DRONEDEK 131; a solid floor 132SF of rollout section; a bracing structure 132B for enclosure 132E for side movement; a means 132DD to drive floor 132SF chain, cable, belt, or the like; a pulley/sprocket 132P for means 132DD; a motor 132FM to raise/lower floor 132F; a means 132DD to drive floor 132F chain, cable, belt or the like; a pulley/sprocket 132P for means 132DD; a means 132DM to support drive floor 132SF at the end where drive means 132DD—enclosed channel, angle with castors or the like; a means 132EM to support drive floor 132SF at opposite end of drive—enclosed channel, angle with castors or the like; a set of rails 132R that hold hot drawer system 234 as it shuttles back and forth into enclosure 132E for side movement of hot drawer; a receptacle 178 for 110 V source, for cellphone charging, and for Tesla, electric scooter, and the like charging; and power source 179 for powered rollers and for Tesla, and scooter charging 178 and the like; a power source 179 for powered rollers and for Tesla, and scooter charging 178 and the like; a motor 232FM to shuttle hot drawer system 234; a hot drawer system 234 that shuttles back and forth into enclosure 132E for side movement of hot drawer; a means 236 to drive hot drawer system 234 back and forth on a set of rails 232R chain, cable, belt or the like to motor 232FM and castors along hot drawer system 234 that move along rails 232R; and a powered hot/cold plate temperature assist 160.

Figure 15:
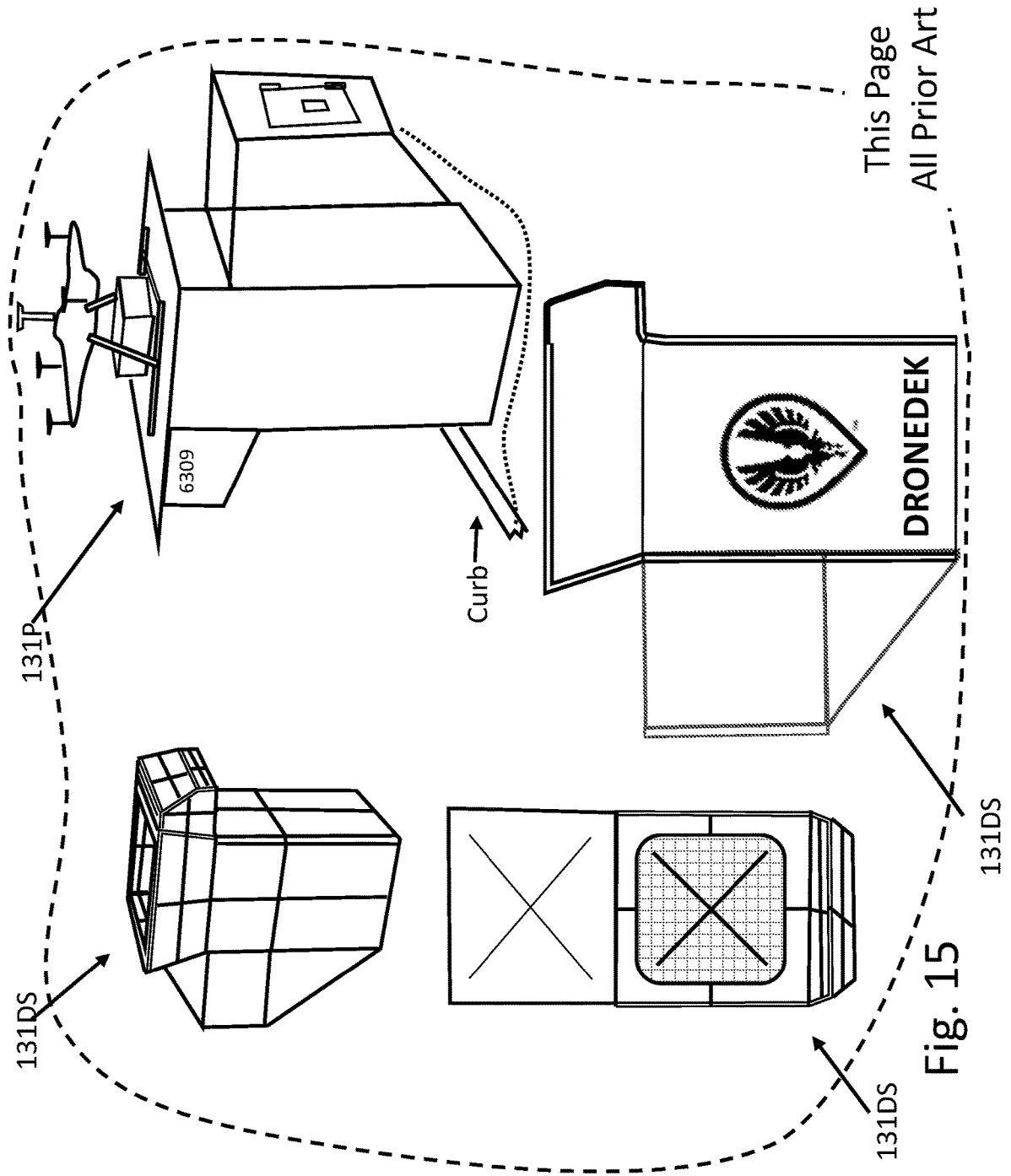
FIG. 15 is a group of sketches and prototype of a docking station/DRONEDEK with the Special Hot and Cold Section drone docking station called a DRONEDEK Temperature Controlled device.

FIG. 15 is a group of prior art sketches 131DS and prototype 131P of a docking station/DRONEDEK with the Special Hot and Cold Section drone docking station called a DRONEDEK Temperature Controlled device 131. Shown here are a prototype 131P of DRONEDEK with Special Hot and Cold Section drone docking station called a DRONEDEK Temperature Controlled device 131. These speak for themselves based on the other drawings herein.

Figure 16:
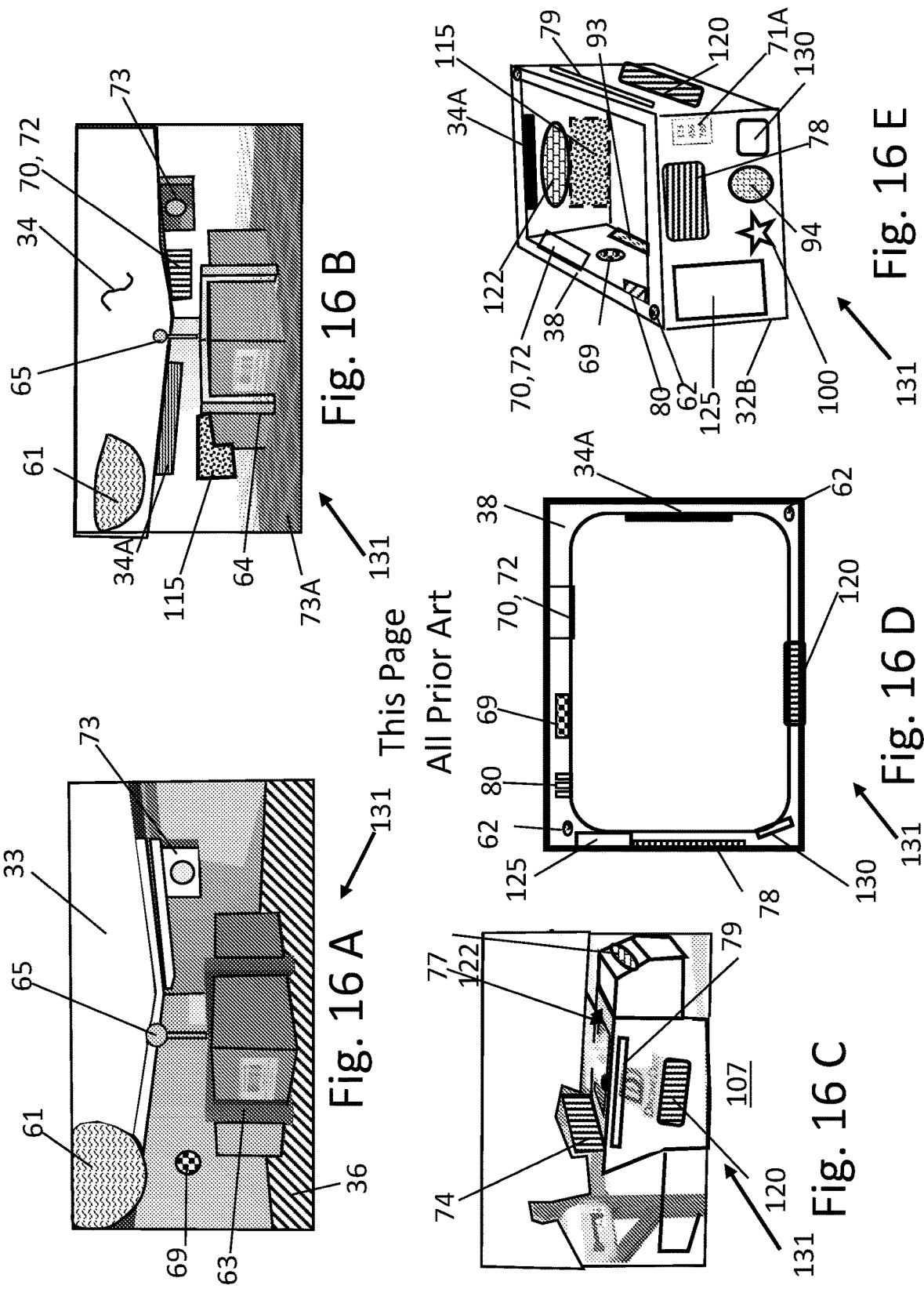
FIG. 16 A through 16 I are sketches of a general embodiment of the Special Hot and Cold Section drone docking station called a DRONEDEK Temperature Controlled device indicating some of the features of the DRONEDEK.
Figure 16:
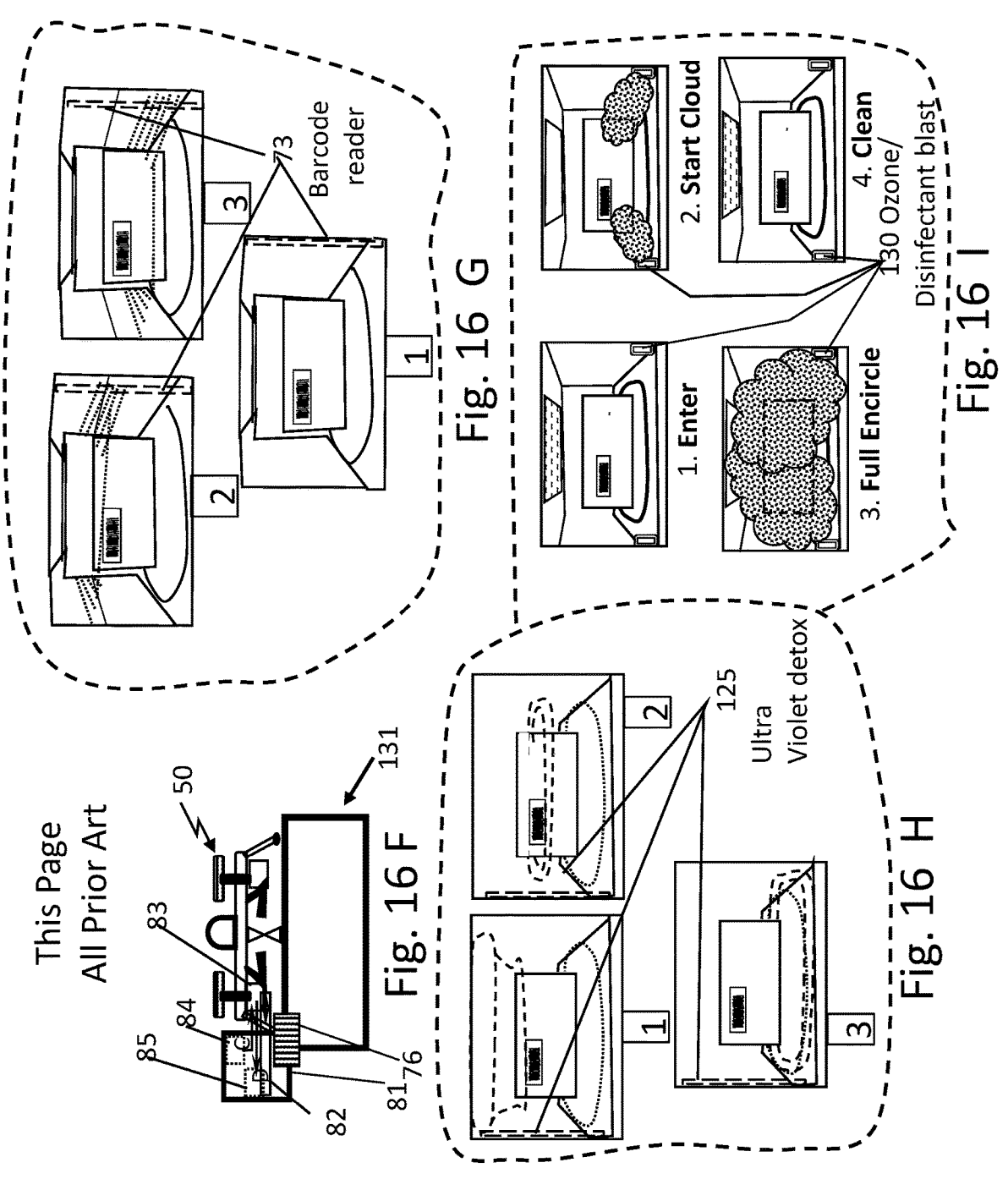

FIG. 16 A through 16 I are prior art sketches of a general embodiment of the Special Hot and Cold Section drone docking station called a DRONEDEK Temperature Controlled device 131 indicating some of the features of the DRONEDEK. Note well that these features are brand new in combination with the device and system for an autonomous mobile robot, drone, and/or courier to deliver, hold, protect, and return parcels for multi-users in both residential and commercial applications. Portrayed here are the following: a drone docking station/DRONEDEK 131 for deposit of items delivered by drone hereinafter referred to as Special Hot and Cold Section drone docking station called a DRONEDEK Temperature Controlled device 131, drone dock, docking station, the box, or drone box for the deposit of items delivered by drone; a drone docking station structure 32 with expanding section/accordion with a raiseable floor 32F; a drone structure/container opening 33; a closeable and openable, movable/motorized sliding or hinged/pivoting doors 34 on the dock structure 32; a door motor 34A; a means 36 to prevent damage and deterioration like a foam or soft padding, a curved side, a sealed door, a temperature controlled interior, and a heated sliding door; a top surface 38 of docking structure 32 surrounding the perimeter of the opening 34; a parcel 40 such as food items, groceries, tools, electronics, documents, and the like; a drone 50; a camera system 61 internal/external to compartment of drone 50 having technology and recognition precision to interconnect to applications for facial recognition of humans and pets; an optional receiving dimples 62 for the drone pads 51; a releasable/locking ball and socket 65 with the package 40 or the like; one or more lighting mechanisms 69 inside the container 32; a means of preserving and securely storing 70 the delivered goods once in the box—i.e. a totally secure solution for home or office drone deliveries of parcels 40; a temperature control 72 hot/cold system; a barcode reader 73—infrared or other; a barcode reader waves and signals 73A; a barcode reader label 73B on package 40; a wind block 74; a charging station 76; a heated top 77; a motion flood light 78 that has focus technology to flood an area or create spotlight floods at specific line of sight areas in the yard near the DRONEDEK 131; a mail slot 79 for regular land mail; a collector panel 80 for detection of explosives or anthrax or other perceived threats; a battery exchange mechanism 81 for interchangeability of drone batteries with the DRONEDEK; an extendable/retractable means for exchanging 82 batteries such as an extendable arm and securing latch to remove the drone battery 83, move it to the exchange mechanism 81 and move charged battery 84 back to drone 50 and re-engage the drone power connection; a drone battery 83; a charged battery 84; a discharged battery 85; a weight and dimension sensors 93; a two-way speakers and loud audio alarm system 94 to communicate to persons at the DRONEDEK 131 or to provide loud alarms, shrill sirens etc.; a location and tracking means 100 of all nearby drones and communication with docking station 131; a specific GPS address 107 for the docking station 131; a return tattoo printer 115 branding of package for return and ability to place gate code 115A to a codex or manual intervention and delivery; micro weather station 120 mechanisms, sensors, etc.; a paint/tag and track 122 monitoring communications and follow with GPS once painted; an ultraviolet detox/disinfect 125; and an ozone detox/disinfect 130 using O3 as a disinfectant/detox material.

A further description of several of these features is appropriate. On the external cameras 61 they have a facial recognition system is a technology capable of identifying or verifying a person from a digital image or a video frame from a video source. There are multiple methods in which facial recognition systems work, but in general, they work by comparing selected facial features from given image with faces within a database. It is also described as a Biometric Artificial Intelligence based application that can uniquely identify a person by analyzing patterns based on the person's facial textures and shape. While initially a form of computer application, it has seen wider uses in recent times on mobile platforms and in other forms of technology, such as robotics. It is typically used as access control in security systems and can be compared to other biometrics such as fingerprint or eye iris recognition systems. Although the accuracy of facial recognition system as a biometric technology is lower than iris recognition and fingerprint recognition, it is widely adopted due to its contactless and non-invasive process. Recently, it has also become popular as a commercial identification and marketing tool. Other applications include advanced human-computer interaction, video surveillance, automatic indexing of images, and video database, among others.

As to a barcode reader 73, a barcode reader (or barcode scanner) is an optical scanner that can read printed barcodes, decode the data contained in the barcode and send the data to a computer. Like a flatbed scanner, it consists of a light source, a lens and a light sensor translating for optical impulses into electrical signals. Additionally, nearly all barcode readers contain decoder circuitry that can analyze the barcode's image data provided by the sensor and sending the barcode's content to the scanner's output port. Barcode readers can be differentiated by technologies as follows: Pen-type reader consist of a light source and photodiode that are placed next to each other in the tip of a pen. To read a barcode, the person holding the pen must move the tip of it across the bars at a relatively uniform speed. The photodiode measures the intensity of the light reflected from the light source as the tip crosses each bar and space in the printed code. The photodiode generates a waveform that is used to measure the widths of the bars and spaces in the barcode. Dark bars in the barcode absorb light and white spaces reflect light so that the voltage waveform generated by the photodiode is a representation of the bar and space pattern in the barcode. This waveform is decoded by the scanner in a manner like the way Morse code dots and dashes are decoded. The Laser scanners work the same way as pen-type readers except that they use a laser beam as the light source and typically employ either a reciprocating mirror or a rotating prism to scan the laser beam back and forth across the barcode. As with the pen-type reader, a photodiode is used to measure the intensity of the light reflected from the barcode. In both pen readers and laser scanners, the light emitted by the reader is rapidly varied in brightness with a data pattern and the photodiode receive circuitry is designed to detect only signals with the same modulated pattern. CCD readers use an array of hundreds of tiny light sensors lined up in a row in the head of the reader. Each sensor measures the intensity of the light immediately in front of it. Each individual light sensor in the CCD reader is extremely small and because there are hundreds of sensors lined up in a row, a voltage pattern identical to the pattern in a barcode is generated in the reader by sequentially measuring the voltages across each sensor in the row. The important difference between a COD reader and a pen or laser scanner is that the CCD reader is measuring emitted ambient light from the barcode whereas pen or laser scanners are measuring reflected light of a specific frequency originating from the scanner itself. LED scanners can also be made using CMOS sensors and are replacing earlier Laser-based readers.

For a collector panel 80: An explosives trace-detection portal machine, also known as a trace portal machine and commonly known as a puffer machine, is a security device that seeks to detect explosives and illegal drugs at airports and other sensitive facilities as a part of airport security screening. The machines are intended as a secondary screening device, used as a complement to, rather than a substitute for, traditional X-ray machines. The term "trace-detection" refers to the machine's ability to detect extremely small "traces" of these compounds. The exact sensitivities of these machines are not available information, but a mass spectrometer detects compounds on a molecular level and would only be limited by the efficiency of the collection from the air puffed to obtain a sample for analysis. Some companies use ion mobility spectrometry (IMS) technology and can detect explosives such as RDX, PETN, TNT, and Nitroglycerin. It can also detect controlled substances such as marijuana, cocaine, heroin, PCP, methamphetamine, and MDMA. One system developed is physically similar but internally different. It uses mass spectrometry (MS) technology, which can detect 16 explosive compounds with 10-100× more sensitivity than IMS, resolve multiple compounds at the same time, and perform shoe bomb detection without removing shoes. This collection technology is also significantly different and offers a narcotics screening portal as a separate product. The machine operates by releasing multiple puffs of air at a passenger who is standing upright within the machine. This will flush out any particles on the person inside the machine then analyze and identify them in seconds. It is capable of screening up to 180 passengers an hour. This sample is then analyzed using IMS or MS technology to search for specific explosive or narcotic compounds. If a substance of concern is detected, the security personnel are notified by a visible and/or audible alarm. The machine can also be used for other bio-hazardous materials associated but not limited to bio- and germwarfare chemicals and biological hazards.

For a micro weather station 120 mechanisms, sensors, etc. consider this background: Used is a novel and practical micro weather station, which can sense temperature, relative humidity, pressure, and anemometer, and is portable in small size and possesses high precisions. The micro weather station comprises multi-sensor chip, anemometer, measurement system, display system and power management system. Based on MEMS technology, multi-sensor chip integrated temperature, relative humidity and pressure is developed and manufactured. A drag force wind sensor using the torque of cantilever to measure the velocity of wind is developed. The wind direction can be measured by perpendicularly encapsulating the two-wind sensor. Compared with those processes used in other types of micro weather station, the processes used is very simple and compatible. All the results exhibit outstanding performances of the micro weather station. Micro-electromechanical systems (MEMS) are a process technology used to create tiny integrated devices or systems that combine mechanical and electrical components. They are fabricated using integrated circuit (IC) batch processing techniques and can range in size from a few micrometers to millimeters. Weather monitoring is of great importance in many domains such as: agriculture, military, entertainment etc. There are several solutions for monitoring the weather. The classical solution consists in static weather stations. Another solution is based on wireless sensor networks (WSNs). The third solution uses low dimensions weather stations. This paper presents a weather station made of temperature, humidity, pressure, and luminosity sensors embedded in a microcontroller-based board. The station is controlled through the SMS service of mobile phones. Weather sensors from micro systems companies are redefining what an all-in-one weather sensor should be. Everything needed for weather sensing is built into one unit. That includes 27 environmental parameters, a processor, communications unit, and solar power system. Small and lightweight, these portable weather sensors take on jobs previously reserved for larger, more complex systems. Within 60 seconds of turning them on, they are ready to transmit local conditions using a cellular or Iridium satellite link. With these advantages in size, weight and ruggedness, our weather sensors are opening new markets and locations for autonomous meteorological sensors. Typical desires for a weather station include (for example and not as a limitation): Cloud-based data logging, solar power, and processor; Two-way Cellular or Iridium satellite connection; Integrated panoramic imaging; Expansion port; Rugged and portable; Easy installation; and Autonomous operations. The Weather Data Collected is typically: Temperature; Barometric pressure; Humidity; Wind speed; Wind direction; Compass reading; Angular tilt; Visibility; Dust accumulation; Lightning distance; Visual imagery; Precipitation amount; Present weather; and GPS location.

A Paint/tag and track 122 monitoring communications considers this: Drones 50 and these docking stations 131 can tag and track quarry using nanoparticle sprays. The US Air Force is funding work to let a drone's tag suspects or cars with a spray that gives them a distinct spectral signature, making them easy to track. On a dusty road in northern Pakistan, a nondescript vehicle rounds a corner. Fifty meters overhead, a tiny drone buzzes unseen, spraying a fine mist across the vehicle's roof as it passes below. The vehicle is now tagged and can be tracked from many kilometers away by an infrared scanner on a larger drone. This scenario may soon be played out now that the US Air Force has contracted to develop a drone-based tagging system. Tagging materials—taggants—are made that can be used to discreetly label vehicles carrying smuggled goods, or people who are involved in civil disobedience or attempting to cross international borders illegally. Interest in tagging technology has been driven in part by growing pressure on the White House over civilian deaths in US drone attacks. Tagging by drones would allow people to be tracked for subsequent arrest. Some taggants are based on quantum dots—semiconductor nanocrystals less than 50 atoms across. Because of quantum effects, they absorb and emit light at specific wavelengths. The company has demonstrated a taggant powder that, when illuminated with an invisible ultraviolet laser, can be detected by infrared cameras 2 kilometers away. The powder is delivered as an aerosol that clings to metal, glass and cloth, and batches can be engineered to have distinct spectral signatures. The nanocrystals would be sprayed by a hand-launched drone with a wingspan of less than 1.5 meters, it is quiet and has a range of several kilometers. A larger Predator drone could then illuminate the target with an ultraviolet laser and track its progress. "Nanocrystals can be sprayed by a hand-launched drone and illuminated with a laser". But spraying the taggant accurately can be tricky. They experimented with small drones that delivered a simulated taggant made from colored sugar beads used in cake decoration. They wanted to coat a road with the stuff so that it would stick to the wheels of any vehicle that drove through. But the wind blew the beads around as soon as they were sprayed. So, the team developed software to model the effects of wind so they could allow for it when spraying When they fed in estimates of wind speed and direction based on readings from the drone's sensors, the drone could hit a target from an altitude of 45 meters. A more advanced system would allow accurate tagging from greater distances, which would be more effective as small drones can be inaudible when flying further than 60 meters away. The US Department of Homeland Security has expressed interest in giving non-lethal offensive capabilities to drones used by its Customs and Border Protection service. Any such move is bound to be contentious, and tagging might prove more acceptable to US public opinion. Drones could also use smart tagging during riots so that the people involved can be identified and later arrested. Many ways to make one's mark—TAGGING technology has moved on since the days of using water cannon with indelible dye to mark rioters. One company produces a range of products containing unique synthetic DNA sequences. These include automatic sprays for marking intruders, a personal defense spray and a device like a paintball pistol that can tag an individual from 30 meters away.

For Ultraviolet detox/disinfect 125 systems: Ultraviolet germicidal irradiation (UVGI) is a disinfection method that uses short wavelength ultraviolet (ultraviolet C or UVC), light to kill or inactivate microorganisms by destroying nucleic acids and disrupting their DNA, leaving them unable to perform vital cellular functions. UVGI is used in a variety of applications, such as food, air, and water purification. UVC light is weak at the Earth's surface as the ozone layer of the atmosphere blocks it. UVGI devices can produce strong enough UVC light in circulating air or water systems to make them inhospitable environments to microorganisms such as bacteria, viruses, molds, and other pathogens. UVGI can be coupled with a filtration system to sanitize air and water. The application of UVGI to disinfection has been an accepted practice since the mid-20th century. It has been used primarily in medical sanitation and sterile work facilities. Increasingly, it has been employed to sterilize drinking and wastewater, as the holding facilities are enclosed and can be circulated to ensure a higher exposure to the UV. In recent years UVGI has found renewed application in air purifiers. UV light is electromagnetic radiation with wavelengths shorter than visible light but longer than X-rays. UV is categorized into several wavelength ranges, with short-wavelength UV (UVC) considered "germicidal UV". Wavelengths between about 200 nm and 300 nm are strongly absorbed by nucleic acids. The absorbed energy can result in defects including pyrimidine dimers. These dimers can prevent replication or can prevent the expression of necessary proteins, resulting in the death or inactivation of the organism.

Mercury-based lamps operating at low vapor pressure emit UV light at the 253.7 nm line.

Ultraviolet light-emitting diodes (UVC LED) lamps emit UV light at selectable wavelengths between 255 and 280 nm.

Pulsed-xenon lamps emit UV light across the entire UV spectrum with a peak emission near 230 nm.

Microorganisms have less protection against UV and cannot survive prolonged exposure to it. A UVGI system is designed to expose environments such as water tanks, sealed rooms and forced air systems to germicidal UV. Exposure comes from germicidal lamps that emit germicidal UV at the correct wavelength, thus irradiating the environment. The forced flow of air or water through this environment ensures exposure. The degree of inactivation by ultraviolet radiation is directly related to the UV dose applied to the water. The dosage, a product of UV light intensity and exposure time, is usually measured in microjules per square centimeter, or equivalently as microwatt seconds per square centimeter (was/cm$^2$). Dosages for a 90% kill of most bacteria and viruses range from 2,000 to 8,000 was/cm$^2$. Larger parasites such as cryptosporidium require a lower dose for inactivation. As a result, the U.S. Environmental Protection Agency has accepted UV disinfection as a method for drinking water plants to obtain cryptosporidium, giardia, or virus inactivation credits. For example, for a 90% reduction of cryptosporidium, a minimum dose of 2,500 µW·s/cm$^2$ is required based on the U.S. EPA UV Guidance Manual published in 2006. The effectiveness of germicidal UV depends on the length of time a microorganism is exposed to UV, the intensity and wavelength of the UV radiation, the presence of particles that can protect the microorganisms from UV, and a microorganism's ability to withstand UV during its exposure. In many systems, redundancy in exposing microorganisms to UV is achieved by circulating the air or water repeatedly. This ensures multiple passes so that the UV is effective against the highest number of microorganisms and will irradiate resistant microorganisms more than once to break them down. "Sterilization" is often misquoted as being achievable. While it is theoretically possible in a controlled environment, it is very difficult to prove, and the term "disinfection" is generally used by companies offering this service as to avoid legal reprimand. Specialist companies will often advertise a certain log reduction, e.g., 6-log reduction or 99.9999% effective, instead of sterilization. This takes into consideration a phenomenon known as light and dark repair (photoreactivation and base excision repair, respectively), in which a cell can repair DNA that has been damaged by UV light. The effectiveness of this form of disinfection depends online-of-sight exposure of the microorganisms to the UV light. Environments where design creates obstacles that block the UV light are not as effective. In such an environment, the effectiveness is then reliant on the placement of the UVGI system so that line of sight is optimum for disinfection. Dust and films coating the bulb lower UV output. Therefore, bulbs require periodic cleaning and replacement to ensure effectiveness. The lifetime of germicidal UV bulbs varies depending on design. Also, the material that the bulb is made of can absorb some of the germicidal rays.

For Ozone detox/disinfect unit 130 utilizing O3 to disinfect: Microorganisms cause issues in various places, in a clinical setting bacterium can cause dangerous outbreaks. Ozone can be used as a chemical disinfectant to kill bacteria and viruses with low ozone concentrations. The contact time is altered depending on the desired deactivation grade. For many applications, a bacteria reduction of 99.99% which corresponds to a 4-log reduction is enough, for a higher deactivation grade the solution is easily adapted to provide higher concentrations and exposure time, in adapted solutions even bacteria spores can be treated. The figure above applies for treatment in rooms and ventilation ducts, that have been used with ozone to limit the spread of airborne microorganisms in food industries and food storage. Non-touch technologies include the usage of UV-lamps and chemicals dispersed as an aerosol or gas which deactivates microorganisms. Compared to other treatment methods for air disinfection, ozone can efficiently disinfect large air volumes, neutralizing micro-organisms, including viruses. This makes it ideal for use in medical applications, for example in hospitals or doctors waiting rooms. An important factor that enables savings is the time the cleaning agent can actively deactivate bacteria. Ozone concentration is adapted to the desired log reduction after finished treatment ozone either decompose into oxygen naturally over several hours or the decomposition is accelerated significantly using ozone destructors.

Figure 17:
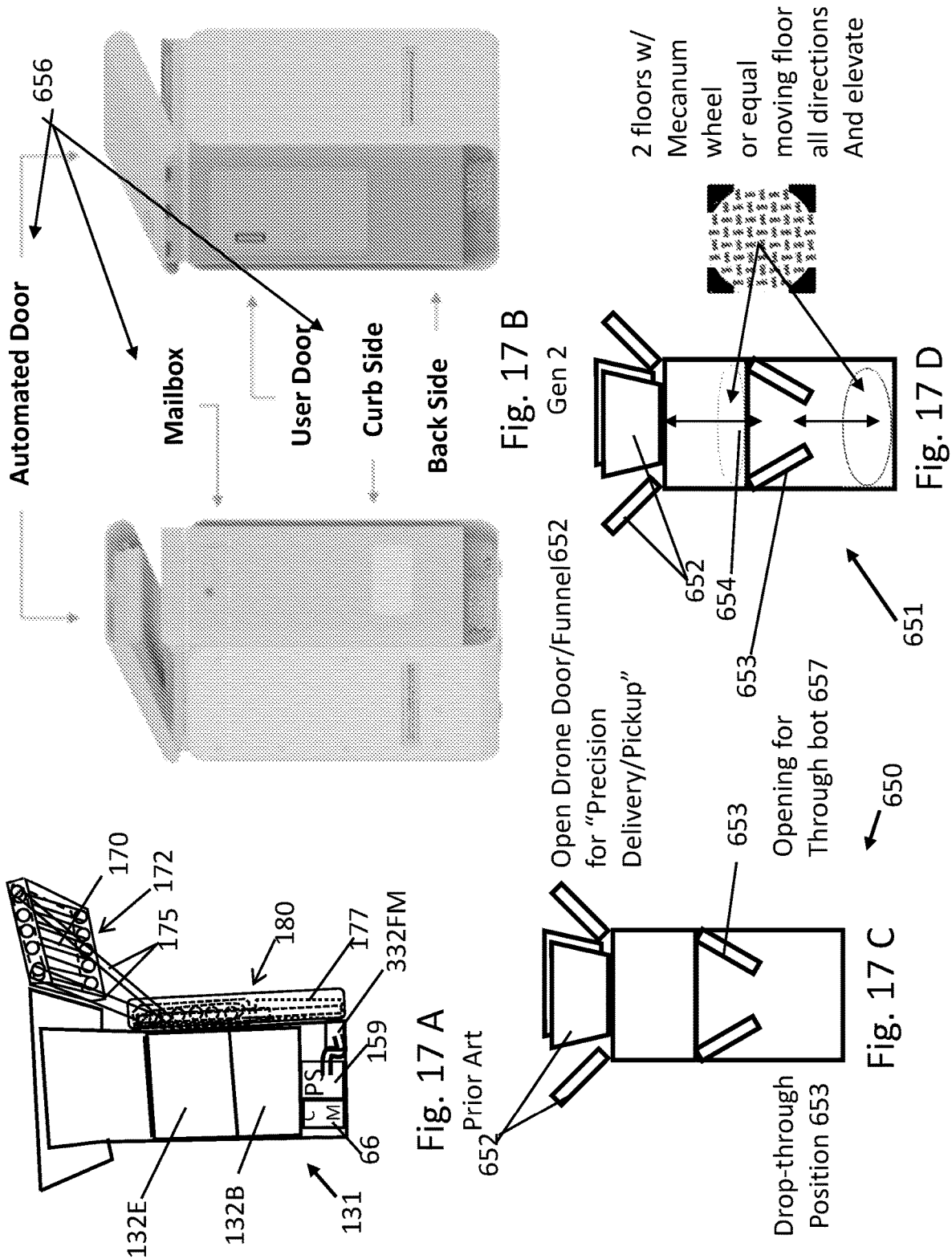
FIGS. 17 A through 17 D are sketches of a prior art assist mechanism for unloading robot/AUVS (automated unmanned vehicle systems) and new manners for loading and unloading a DRONEDEK docking station.

FIGS. 17 A through 17 D are sketches of parcel moving systems. A prior art assist mechanism 131 is shown for unloading robot/AUVS (automated unmanned vehicle systems) and new manners for loading and unloading a DRONEDEK docking station. Demonstrated by these drawings are: a drone docking station/DRONEDEK 131 for deposit of items delivered by drone hereinafter referred to as Special Hot and Cold Section drone docking station called a DRONEDEK Temperature Controlled Device, drone dock, docking station, the box, or drone box for the deposit of items delivered by drone; a powered rollers 170 for assist platform 172; an assist platform 172; an extending support arms 175; an extension cylinder 177 for robot/AUVSI assist unit 180; a power source 159; a robot/AUVS (automated unmanned vehicle systems) assist unit 180 to assist unload of parcels 40 to DRONEDEK 131; and a motor and hydraulic unit 332 FM to robot/AUVSI assist unit 180. FIGS. 17 B through 17 D show new art with: a device and system 650 to Deliver, Hold, Protect, and Return Parcels for multiusers residential and commercial application with top funnel/parcel directors and drop through features; a device and system 651 to Deliver, Hold, Protect, and Return Parcels for multiusers residential and commercial application; a funnel/parcel directors 652 features such as fold out extensions and portions of the top of the DRONEDEK docking station that can be opened to various angles and help direct the parcels for receiving or sending drop through features 653 for loading through bots that literally can roll under the docking station; a top drone deck landing pad 654—with features to use the corner elevators to traverse up and down (elevate) and with omni-directional powered Mecanum wheels or equal like a moving floor to move parcels in all directions for moving to cubicle storage bins and/or third-party systems for a locker box storage; a bottom conveyor turntable pad 655—with features to use the corner elevators to traverse up and down (elevate) and with omni-directional powered Mecanum wheels or equal like a moving floor to move parcels in all directions for moving to cubicle storage bins and/or third-party systems for a locker box; and features 656 of GEN 2 Dronedek including automated hinged or sliding door, mailbox, side user door for unloading and maintenance and the orientation of curbside and back side indicated. Also note the Opening for Through bot to roll under and load/unload parcels 657.

Figure 18:
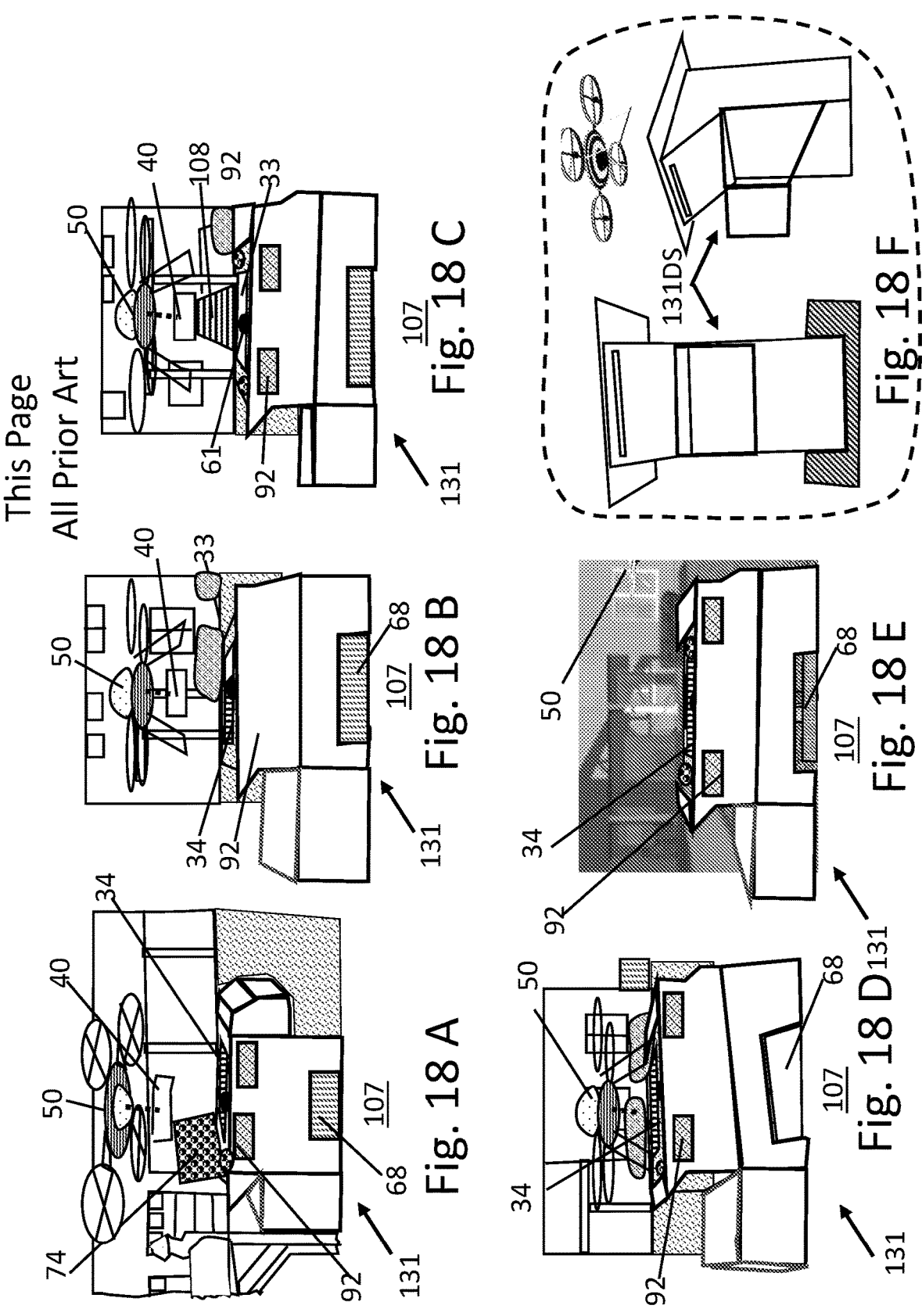
FIG. 18 A through 18 H are sketches of the operation of delivery by a drone at the residential or commercial receiving location and the DRONEDEK with a Special Hot and Cold Section drone docking station called a DRONEDEK Temperature Controlled device.
Figure 18:
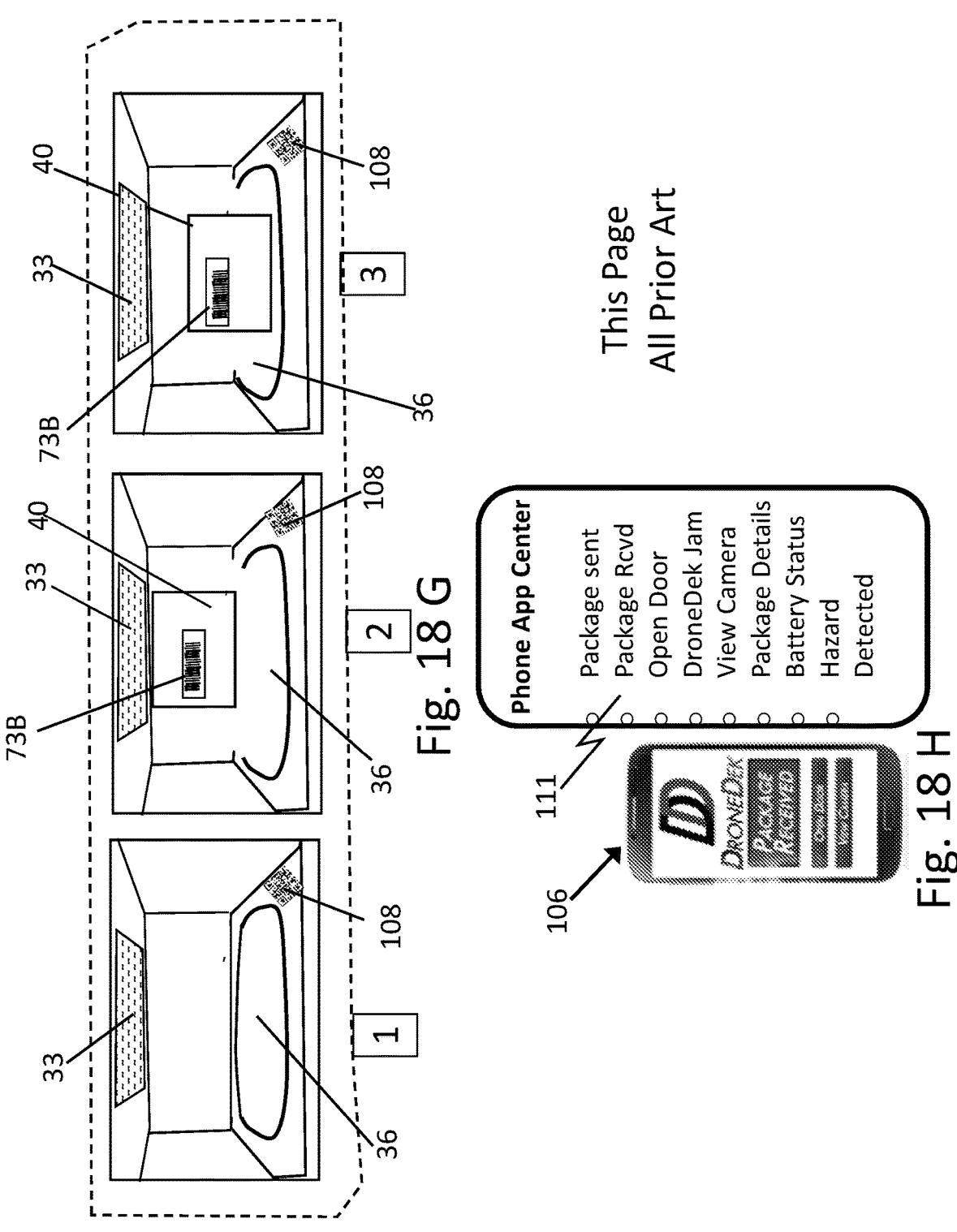

FIG. 18 A through 18 H are sketches of the operation of delivery by a drone 50 at the residential or commercial receiving location 107 and the DRONEDEK 131 with a Special Hot and Cold Section drone docking station called a DRONEDEK Temperature Controlled device. This section is described below in the Operations Section.

Figure 19:
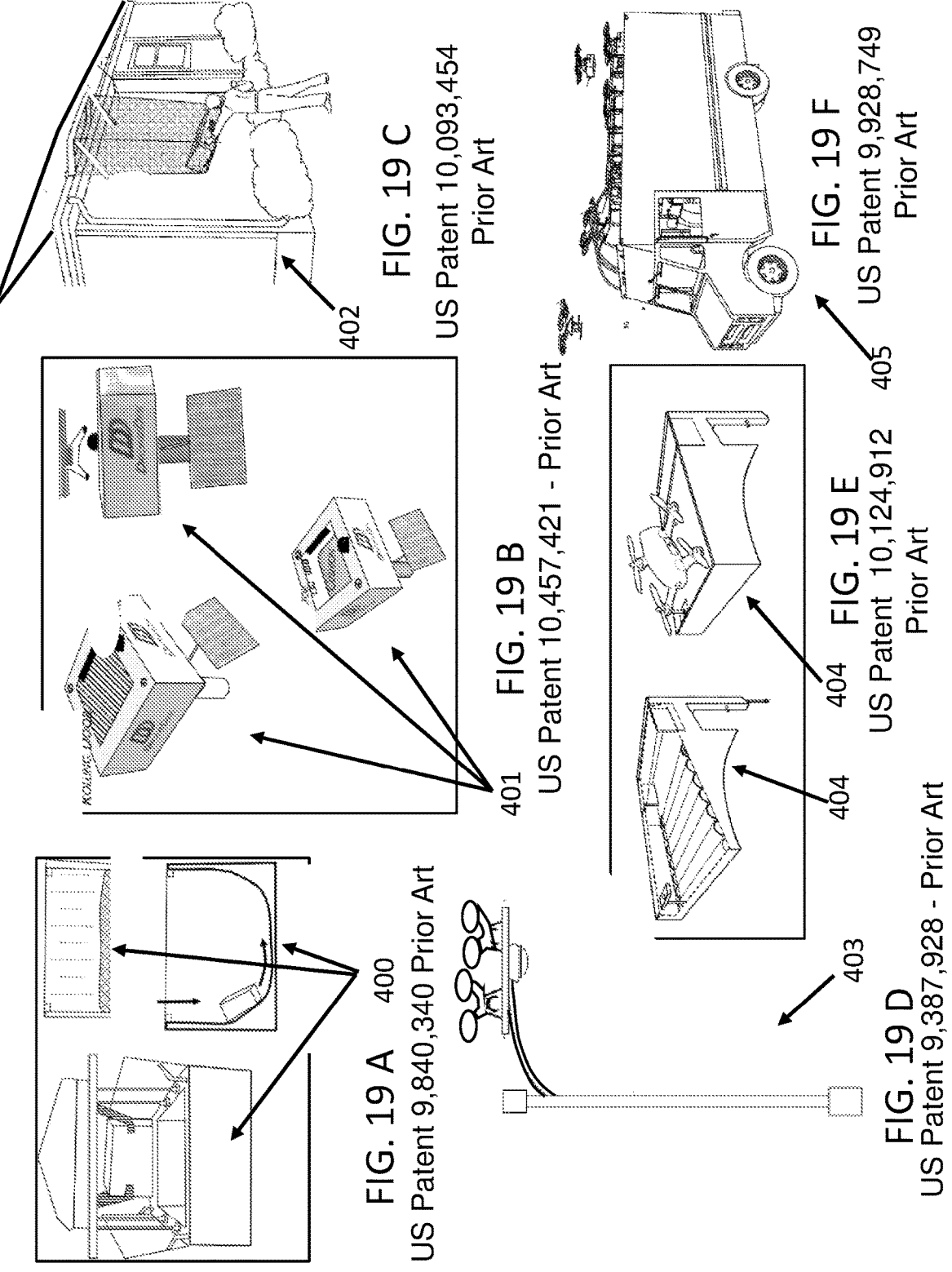
FIG. 19 A through 19 F are sketches of prior art in drone delivery systems to date.

FIG. 19 A through 19 F are sketches of prior art in drone delivery systems to date. Here former patents and applications for various docking station and systems are shown. These include: a prior art 400 U.S. Pat. No. 9,840,340 to O'Toole in 2017 named Drone docking station and delivery system; a prior art 401 U.S. Pat. No. 10,457,421 to O'Toole in 2019 named a Drone docking station and delivery system; a prior art 402 U.S. Pat. No. 10,093,454 to Kalyan in 2018 entitled a Unmanned aerial vehicle payload receiving apparatus; a prior art 403 U.S. Pat. No. 9,387,928 to Gentry et al in 2016 called a Multi-use UAV docking station systems and methods; a prior art 404 U.S. Pat. No. 10,124,912 to Walsh in 2018 called a Landing pad for unmanned aerial vehicle delivery; and a prior art 405 U.S. Pat. No. 9,928,749 to Gil et al in 2018 entitled Methods for delivering a parcel to a restricted access area. As can be seen, the Special Hot and Cold Section drone docking station called a DRONEDEK Temperature Controlled device 131 is a unique combination and use as described herein.

The objects of the device include but are not limited to Objects: 1. To provide for communication between the drone dock and a drone, 2. To provide security, and preservation of the delivered goods before during and after delivery, and 3. To provide expansion of the secure retention area for accepting several deliveries.

Features include:

| | |
|---|---|
| Security | Has a secure opening and closing door feature that allows the drone to communicate with the station and open and close its cargo doors to receive and ship its contents - means for locking 71 and a keypad 71A for onsite access to the DRONEDEK. |
| Hot and Cold Temperature sections | Provides temperature control for the holding section 234 to provide both a hot and cold holding section for multiple parcels whereby Dual drawers - hot/cold - drawer on front with bottom compartment is cold, above is hot so there is a temperature controlled Hot cargo bay; and Cold cargo bay by way of a powered hot/cold plate temperature assist 160. |
| Protection from explosions, disease, etc. | collector panel 80 for detection of explosives or anthrax or other perceived threats. |
| Weather data station | micro weather station 120 mechanisms, sensors, etc. |
| Intercommunications with drones and UAV | location and tracking means 108, 100, 110 of all nearby drones and communication with docking station 131. Able to have encrypted communication and tracking of driverless vehicles, robots, vendors that interact with drones. DRONEDEK to utilize non station drone delivery features including vehicle and commercial carriers and mobile DRONEDEK applications; provides the ability to track and interface with aerial, driverless cars, or robots (i.e., full UAV, drone and robotic |
| Data retrieval | Interchanges information with providers and collects information for Big Data Collection and Networking for marketing information and data. |
| Disease and virus removal | ozone detox/disinfect 130 and ultraviolet detox/disinfect 125. |
| Tracking assist | camera system 61 internal/external to compartment of drone 50 having technology and recognition precision to interconnect to applications for facial recognition of humans and pets and paint/tag and track 122 monitoring communications and follow the items with GPS once painted. |
| Mobile Units | This accommodates a mobile unit 199 to place the unit where it is needed or wanted. |
| Assist to unload | robot/AUVS (automated unmanned vehicle systems) assist unit 180 to assist unload of parcels 40 to DRONEDEK 131. |
| Preservation | a means of preserving and securely storing 70 the delivered goods once in the box - i.e., a totally secure solution for home or office drone deliveries of parcels 40 and a temperature control 72 hot/cold system. |

-continued

| Local Security Features | At the location of the DRONEDEK docking station 131 it provides flood lights, two-way speakers, dog whistle, loud audio alarms 94, and flashing and colored LED lighting 92 for security and communications and for alerting emergency vehicles and first responders |
|---|---|
| Weatherproof | Protects packages from rain, wind, sleet, hail and snow, and harsh temperatures. A heated cargo door option allows for access during the iciest of weather. |
| GPS Location Enabled | Allows through a GPS beacon for the shipping drone to home in on the DRONEDEK's precise location. |
| Charging Station | Features a built-in charging station that can re-energize the drone, effectively doubling drone delivery range- charging station 76 and battery exchange mechanism 81 for interchangeability of drone batteries with the DRONEDEK. |
| Solar Powered | Is powered by a solar panel and/or 110-volt electrical power supply, allowing for operation of its high-level features - solar panel 68 as a power source. |
| Drop Off and Pick Up | Is a secure receptacle designed to hold parcels that are received or that are waiting to be shipped - a weight and dimension sensors 93, a barcode reader 73 - infrared or other, and a return tattoo printer 115 branding of package for return and ability to place gate code 115A to a codex or manual intervention and delivery, can mark a gate code 115A onto the carton 40 for manual delivery. |
| Flexible installation | Has a secure mounting 39A infrastructure for iron-clad installation to a structure or concrete flat surface. |
| Connectivity | Allows the user to easily stay connected to his/her package. DRONEDEK features a contents-sensing switch that via its app, can communicate successful receipt and shipping of parcels to shipper, recipient, and/or shipping company. A user can even see the package via DRONEDEK's built-in camera 61. |
| Remote Access | Features a secure mobile application allowing for remote camera access and the ability to lock and unlock ones DRONEDEK via one's phone or tablet. The owner of the box may retrieve the contents easily through a simple code entered, key or cell phone application 111. |

The Big Data Collection anticipates using blockchain technology. A simple explanation of this is that a block in a blockchain is a collection of data. The data is added to the block in blockchain, by connecting it with other blocks in chronological others creating a chain of blocks linked together. The first block in the Blockchain is called Genesis Block. A blockchain is a decentralized, distributed, and public digital ledger that is used to record transactions across many computers so that any involved record cannot be altered retroactively, without the alteration of all subsequent blocks. A blockchain has been described as a value-exchange protocol. With the paint/tag and track 122, camera system 61, GPS location 107, and data track 108 features and resultant data, by providing the data from the Dronedek receptacles and connecting the receptacles data reservoir to various emergency systems and application, the proper authorities can be alerted and assisted to report emergency events and can help direct/guide authorities to building locations or even locations of vehicles and persons.

The details mentioned here are exemplary and not limiting. Other specific components and manners specific to describing a device and system to Deliver, Hold, Protect, and Receive Parcels for multi-users residential and Commercial applications—a/k/a Cluster Box for various applications may be added as a person having ordinary skill in the field of the art of drone docking station and package receptacles for drone or unmanned aerial vehicle (UAV), robotic carriers, or automated unmanned vehicle systems (AUVS) devices and their uses well appreciates.

Operation of the Preferred Embodiment

The device and system to Deliver, Hold, Protect, and Receive Parcels for multi-users residential and Commercial applications—a/k/a Cluster Box for various applications has been described in the above embodiment. The manner of how the device operates is described below. One notes well that the description above and the operation described here must be taken together to fully illustrate the concept. The preferred embodiment of the device and system to Deliver, Hold, Protect, and Receive Parcels for multi-users residential and Commercial applications—a/k/a Cluster Box for various applications comprising: At least one set of Chambers 545 with series of multi-belt transfer conveyors 537, and a series of 90-degree roller turns 542 and a flip chute/diverter 547; (b) a 4-post elevator 535; (c) a table sorter 540; and (d) a receiving door 550, a rest platform 552 for parcel 40, and a set 560 of communication and power controls.

The device and system to Deliver, Hold, Protect, and Receive Parcels for multi-users residential and commercial applications operates as depicted in FIGS. 2 through 6 in the drawings. Essentially, a secure encrypted code 110 that drone 50 accesses to direct the docking station to open its top to allow for safe delivery into the box 530 may be employed. In lieu of code drone may trigger opening of drone dock by simply accessing its landing base. Final communication between the drone and the drone dock 530 may be through electronic or magnetic connection that is made upon the drone landing and connecting with the box. The communication may be directly between the docking or delivery box and the drone itself upon docking in order to facilitate the transmission of a code in a lock box. In alternative embodiments a remote server may be employed whereby the drone communicates its location and docking details to the remote server, upon which the remote server pings or otherwise delivers and signal directly to the box or an associated IP address triggering it to unlock and open. The box may also communicate via RFID to identity itself to the drone (or vice versa) and communicate a bar code or I.D. sequence required for docking and unlocking. In similar fashion a Bluetooth signal may be employed to communicate a code to the drone once the drone is in range of the box and its blue tooth signal. In certain embodiments the box will deliver GPS guidance to the drone for proper docking and delivery into box. Upon successful deposit in the dock, the top will close securely assuring that entry into the dock by vandals, thieves or animals is prohibited. Retrigger to close may be accomplished in similar fashion to the signal to open either by direct communication between the drawing and the box or through a remote server. The box may also be designed to automatically close and lock once the drone un-docks from the box. And the communication may also be turn over a wireless network such as Wi-Fi, Bluetooth satellite etc. and others that would be recognized by those skilled in the art. The communication may be directly between the docking or delivery box and the drone itself upon docking to facilitate the transmission of a code in a lock box. In alternative embodiments a remote server may be employed whereby the drone communicates its location and docking details to the remote server, upon which the remote server pings or otherwise delivers and signal directly to the box or an associated IP address triggering it to unlock and open. The box may also communicate via RFID to identity itself to the drone (or vice versa) and communicate a bar code 73 or I.D. sequence required for docking and unlocking. In similar fashion a Bluetooth signal may be employed to communicate a code to the drone once the drone is in range of the box and its blue tooth signal. In certain embodiments the system 530 will deliver GPS guidance to the drone for proper docking and delivery into box. Upon successful deposit in the dock, the top will close securely assuring that entry into the dock by vandals, thieves or animals is prohibited. Retrigger to close may be accomplished in similar fashion to the signal to open either by direct communication between the drawing and the box or through a remote server. The box may also be designed to automatically close and lock once the drone un-docks from the box.

The system 530 design may allow a drop of the item 40 into its cavity 33 and onto a turntable or elevator. The parcel then is moved through the system by the multi-belt conveyors, turns and diverters. The parcel 40 is then retained until a user requests its retrieval. At that point the parcel 40 is transported through the multi-belt conveyors and elevator to the parcel pick-up window 552 where the user has coded into the system, identifies himself and retrieves the parcel. Shipping of returned packages occur in a reverse manner.

FIGS. 18 A through 18 H are sketches of the operation of delivery by a drone 50 at the residential or commercial receiving location 107 and the prior art Special Hot and Cold Section drone docking station called a DRONEDEK Temperature Controlled device 131. Note well that these features are brand new in combination with the device and system for an autonomous mobile robot, drone, and/or courier to deliver, hold, protect, and return parcels for multi-users in both residential and commercial applications. Shown here are: a drone docking station/DRONEDEK 131 for deposit of items delivered by drone hereinafter referred to as Special Hot and Cold Section drone docking station called a DRONEDEK Temperature Controlled device 131, drone dock, docking station, the box, or drone box for the deposit of items delivered by drone; a drone structure/container opening 33; a closeable and openable, movable/motorized sliding or hinged doors 34 on the dock structure 32; a foam or soft padding 36; a parcel 40 such as food items, groceries, tools, electronics, documents, and the like; a drone 50; a camera system 61 internal/external to compartment of drone 50 having technology and recognition precision to interconnect to applications for facial recognition of humans and pets; an optional receiving dimples 62 for the drone pads 51; a solar panel 68 as a power source; a barcode reader 73—infrared or other; a barcode reader waves and signals 73A; a barcode reader label 73B on package 40; a wind block 74; an external lighting 92 that can be LED type systems to strobe, flash colors, communicate to authorities, distress, etc.; a personal communication devices 106—such as smart phones, tablets, laptops, personal computers, and the like; a specific GPS address 107 for the docking station 131; local signal/or mechanical means 108—to facilitate final location and transfer such as Cold beam technology, Laser beam, Radar, Lidar, Quick Response (QR) code tags, Radio frequency RFID) remote identification tracking and sensing for drone authentication and landing for navigating the drone 50 to its exact location on the docking station 131; and a smart phone application 111 or the like to communicate status of the docking event with the user of the personal communication devices 106. Shipping and receiving by the drones are Coordinated with the FAA, sender, and receiver of the goods 91 when a package is sent or received. Any conflicts send an indicator/warning signal to the smart phone (FIG. 8 H) as well as when items are being received and shipped. If a problem occurs for receiving such as an oversize package or full receptacle 30,131, a message is sent, and the package is sent to a pre-arranged overflow zone. Every Dronedek receptacle 30,131 has what is called the drone zone which is an overflow area for items that are too large or non-functioning DroneDek or that a receptacle is full and there is an electronic surveillance at the zone which monitors packages dropped in those areas. The client is notified that the package is there and if somebody breaks that field and takes that item there is a photo/video and electronic visual documentation of that person. At the zone, an audible alarm "warning one that he/she is too close to the package, please step back or the alarm will sound" is present like the Viper alarm system RTM for vehicles.

Various users are anticipated for the device and system to Deliver, Hold, Protect, and Receive Parcels for multi-users residential and Commercial applications—a/k/a Cluster Box for various applications. For example, and not as a limitation, these include:

| Item | User |
|---|---|
| 1 | Neighborhood |
| 2 | Commercial |
| 3 | Campus and University |
| 4 | Hospitals and Clinics |
| 5 | Military |
| 6 | Trailer Parks |
| 7 | Condominiums |
| 8 | Cluster of customers |

With this description it is to be understood that the device and system to Deliver, Hold, Protect, and Receive Parcels for multi-users residential and Commercial applications—a/k/a Cluster Box for various applications is not to be limited to only the disclosed embodiment of product. The features of the device and system are intended to cover various modifications and equivalent arrangements included within the spirit and scope of the description.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present inventions, the preferred methods and materials are now described above in the foregoing paragraphs.

Other embodiments of the invention are possible. Although the description above contains much specificity, these should not be construed as limiting the scope of the invention, but as merely providing illustrations of some of the presently preferred embodiments of this invention. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

The terms recited in the claims should be given their ordinary and customary meaning as determined by reference to relevant entries (e.g., definition of "plane" as a carpenter's tool would not be relevant to the use of the term "plane" when used to refer to an airplane, etc.) in dictionaries (e.g., widely used general reference dictionaries and/or relevant technical dictionaries), commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used herein in a manner more expansive than its ordinary and customary meaning, the term should be given its ordinary and customary meaning plus the additional expansive meaning, or (b) if a term has been explicitly defined to have a different meaning by reciting the term followed by the phrase "as used herein shall mean" or similar language (e.g., "herein this term means," "as defined herein," "for the purposes of this disclosure [the term] shall mean," etc.). References to specific examples, use of "i.e.," use of the word "invention," etc., are not meant to invoke exception (b) or otherwise restrict the scope of the recited claim terms. Other than situations where exception (b) applies, nothing contained herein should be considered a disclaimer or dis-avowal of claim scope. Accordingly, the subject matter recited in the claims is not coextensive with and should not be interpreted to be coextensive with any particular embodiment, feature, or combination of features shown herein. This is true even if only a single embodiment of the particular feature or combination of features is illustrated and described herein. Thus, the appended claims should be read to be given their broadest interpretation in view of the prior art and the ordinary meaning of the claim terms.

Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques. The present invention contemplates modifications as would occur to those skilled in the art. While the disclosure has been illustrated and described in detail in the figures and the foregoing description, the same is to be considered as illustrative and not restrictive in character, it being understood that only selected embodiments have been shown and described and that all changes, modifications and equivalents that come within the spirit of the disclosures described. heretofore and or/defined by the following claims are desired to be protected.

What is claimed is:

1. A device and system for protecting and holding parcels for a group of multi-users in both a residential and commercial application, comprising:
   (a) at least one set of Chambers having a series of multi-belt transfer conveyors, a series of 90-degree roller turns, and a flip chute/diverter;
   (a) at least one set of Chambers (545) with series of multi-belt transfer conveyors (537), and a series of 90-degree roller turns (542) and a flip chute/diverter (547);
   (b) a 4-post elevator (535);
   (c) a table sorter (540); and
   (d) a receiving door, a rest platform for placing a parcel, and a set of communication and power controls;
   wherein the parcel or parcels are delivered by, and/or returned to an autonomous robot, drone, and/or courier.

2. The device and system (530) described in claim 1, wherein the means for securely storing the goods/parcels once transferred to the interior of the structure of the drone dock is selected from the group consisting of a keypad for onsite access to the drone dock, a facial recognition camera, and a fingerprint activated release system.

3. The device and system (530) described in claim 1, wherein means for locating the drone dock with GPS and then for permitting the drone to accurately approach and to dock with the station is selected from a group consisting of cold beam technology, laser beam, radar, lidar, Quick Response (QR) code tags, and radio frequency identification (RFID).

4. The device and system (530) described in claim 1, wherein the means of encrypted communication between the drone and the drone dock is selected from the group consisting of Wi-Fi, Bluetooth, hot spot, and satellite systems and wherein the drone dock has encrypted communication and tracking of a driverless vehicles, a robots, and vendors that interact with the drone dock and wherein the drone dock can track and interface with an aerial drone, a commercial carrier, a driverless car (UAV) and a robot.

5. The device and system (530) described in claim 1, wherein the optional features are selected from the group consisting of a charging station for drone batteries, an exchange mechanism for a drone battery, a charging station for a cellular telephone, a charging station for an electric scooter, a charging station for an electric bike and a charging station for an electric vehicle.

6. The device and system (530) described in claim 1, wherein the optional feature is a collector to identify explosive material, biohazards, illegal drugs, and anthrax.

7. The device and system (530) described in claim 1, wherein the optional feature is an ultraviolet scan system to eradicate disease, virus and harmful materials.

8. The device and system (530) described in claim 1, wherein the optional feature is an ozone applicator to eradicate disease, virus and harmful materials.

9. The device and system (530) described in claim 1, wherein the set of identification features are a barcode reader and a Quick Response (QR) reader.

10. The device and system (530) described in claim 1, wherein the set of identification features include a weight and dimension sensor, barcode reader, and QR reader.

11. The device and system (530) described in claim 1, wherein the set of identification feature is a tattoo printer for reverse logistics for return of parcels.

12. The device and system (530) described in claim 1, wherein an additional feature on the drone dock is a weather monitoring system.

13. The device and system (530) described in claim 1, wherein an additional feature on the drone dock is a tag and track component to track vehicles and packages.

14. The device and system (530) described in claim 1, wherein an additional feature on the drone dock is a camera with facial recognition software to track humans and pets.

15. The device and system (530) described in claim 1, wherein an additional feature on the drone dock is an encoded chip track to track a lost drone dock receptacle.

16. The device and system (530) described in claim 1, wherein the local feature is a set of two-way speakers with a dog whistle and wherein the speakers can emit loud sirens to alert emergency vehicles and first responders.

17. The device and system (530) described in claim 1, wherein the local feature is a set of LED lights that are colored and can strobe flash and wherein the LED lights can alert emergency vehicles and first responders.

18. A device and system for protecting and holding parcels for a group of multi-users in both a residential and commercial application, comprising: at least one set of Chambers having a series of multi-belt transfer conveyors, a series of 90-degree roller turns, and a flip chute/diverter;

(a) at least one set of Chambers (545) with series of multi-belt transfer conveyors (537), and a series of 90-degree roller turns (542) and a flip chute/diverter (547);

(b) a 4-post elevator (535);

(c) a table sorter (540);

(d) a drop through component (653);

(e) a set of director funnel and doors (652); and (f) a receiving door, a rest platform for placing parcels, and a set (560) of communication and power controls; wherein the parcel or parcels are delivered by, and/or returned to an autonomous robot, drone, and/or courier.

19. A device and system for protecting and holding parcels for a group of multi-users in both a residential and commercial application, comprising: at least one set of Chambers having a series of multi-belt transfer conveyors, a series of 90-degree roller turns, and a flip chute/diverter;

(b) a 4-post elevator (535);

(c) a table sorter (540);

(d) a top drone deck (654) which elevates up and down the 4-post elevator (535) and having a set of omni-directional powered wheels on the deck to direct a parcel (40);

(e) a top drone deck landing pad (654) which elevates up and down the 4-post elevator (535) and having a set of omni-directional powered wheels on the top drone deck to direct the parcel (40);

(f) a bottom conveyor turntable pad (655) which elevates up and down the 4-post elevator (535) and having a set of omni-directional powered wheels on the turntable pad to direct a parcel (40); and (g) a receiving door, a rest platform for placing parcels, and a set of communication and power controls; wherein the parcel or parcels are delivered by, and/or returned to an autonomous robot, drone, and/or courier.

\* \* \* \* \*